US012576246B2

(12) United States Patent
Mr et al.

(10) Patent No.: US 12,576,246 B2
(45) Date of Patent: Mar. 17, 2026

(54) CATHETER SYSTEM HAVING A GUIDEWIRE SLIDER

(71) Applicant: Becton, Dickinson and Company, Franklin Lakes, NJ (US)

(72) Inventors: Karthik Mr, Bangalore (IN); Balaji Kannan, Tamil Nadu (IN); Sakthivel Karthikeyan, Coimbatore (IN); Jeevan Deshpande, Bengaluru (IN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 845 days.

(21) Appl. No.: 17/834,723

(22) Filed: Jun. 7, 2022

(65) Prior Publication Data

US 2023/0390532 A1     Dec. 7, 2023

(51) Int. Cl.
| | |
|---|---|
| *A61M 25/06* | (2006.01) |
| *A61M 25/00* | (2006.01) |
| *A61M 25/01* | (2006.01) |
| *A61M 25/09* | (2006.01) |

(52) U.S. Cl.
CPC .... *A61M 25/0625* (2013.01); *A61M 25/0014* (2013.01); *A61M 25/0097* (2013.01); *A61M 25/0102* (2013.01); *A61M 25/0606* (2013.01); *A61M 25/0693* (2013.01); *A61M 25/0618* (2013.01); *A61M 25/09041* (2013.01)

(58) Field of Classification Search
CPC .......... A61M 25/0102; A61M 25/0606; A61M 25/09041
See application file for complete search history.

(56) References Cited

U.S. PATENT DOCUMENTS

| | | | |
|---|---|---|---|
| 1,962,037 | A | 6/1934 | Schofer |
| 5,501,675 | A | 3/1996 | Erskine |
| 5,704,914 | A * | 1/1998 | Stocking ........... A61M 25/0606 604/195 |
| 6,197,001 | B1 | 3/2001 | Wilson et al. |
| 8,721,546 | B2 | 5/2014 | Belson |
| 9,675,784 | B2 | 6/2017 | Belson |
| 11,471,648 | B2 * | 10/2022 | Hulvershorn ..... A61M 25/0631 |

(Continued)

FOREIGN PATENT DOCUMENTS

| | | | | |
|---|---|---|---|---|
| WO | | 2016178974 A1 | 11/2016 | |
| WO | WO-2020109448 A1 * | 6/2020 | ........ A61M 25/0113 |
| WO | WO-2021166960 A1 * | 8/2021 | ............ A61M 25/06 |

*Primary Examiner* — Nathan R Price
(74) *Attorney, Agent, or Firm* — Kirton McConkie; Whitney Blair; Kevin Stinger

(57)     ABSTRACT

A catheter system may include a catheter hub, a catheter tube, a needle carrier, a needle extending distally from the needle carrier and through the catheter tube, a guidewire slider, and a guidewire extending distally from the guidewire slider. The guidewire slider may be configured to couple to the needle carrier in response to sliding of the guidewire slider. The catheter system may include a safety slider configured to slide with the guidewire slider from a proximal position to a distal position. In response to the guidewire slider and the safety slider sliding together from the proximal position to the distal position, the safety slider may be configured to couple to a proximal end of the needle carrier. In response to rotation of an additional slider into a cutout tab of a housing, the guidewire slider may be configured to uncouple from the additional slider.

9 Claims, 23 Drawing Sheets

(56) References Cited

U.S. PATENT DOCUMENTS

| | | | |
|---|---|---|---|
| 12,274,835 B2 * | 4/2025 | Khoo ................ | A61M 25/0014 |
| 2010/0210934 A1 * | 8/2010 | Belson ............... | A61B 17/3421 |
| | | | 604/164.11 |
| 2011/0282285 A1 * | 11/2011 | Blanchard ......... | A61M 25/0097 |
| | | | 604/164.08 |
| 2016/0206858 A1 * | 7/2016 | Ishida ............. | A61M 25/09041 |
| 2017/0087338 A1 | 3/2017 | Belson | |
| 2020/0078566 A1 | 3/2020 | Mitchell et al. | |
| 2021/0154439 A1 | 5/2021 | Blanchard et al. | |
| 2022/0387761 A1 * | 12/2022 | Ishida ............... | A61M 25/0097 |

* cited by examiner

CATHETER SYSTEM HAVING A GUIDEWIRE SLIDER

BACKGROUND

A common type of catheter assembly includes a peripheral intravenous catheter ("PIVC") that is over-the-needle. As its name implies, the PIVC that is over-the-needle may be mounted over an introducer needle having a sharp distal tip. The catheter assembly may include a catheter adapter, the PIVC extending distally from the catheter adapter, and the introducer needle extending through the PIVC. The PIVC and the introducer needle may be assembled such that the distal tip of the introducer needle extends beyond the distal tip of the PIVC with the bevel of the needle facing up away from skin of the patient immediately prior to insertion into the skin. The PIVC and the introducer needle are generally inserted at a shallow angle through the skin into a blood vessel of the patient.

In order to verify proper placement of the introducer needle and/or the PIVC in the blood vessel, a clinician may confirm that there is flashback of blood in a flashback chamber of the catheter assembly. In some instances, blood may travel into the introducer needle and then out of a flashback notch in the introducer needle to reach the flashback chamber, where the blood is visible to the clinician. Once placement of the introducer needle has been confirmed by observation of the blood, the clinician may remove the introducer needle, leaving the PIVC in place in the blood vessel for future blood withdrawal or fluid infusion.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to a catheter system having a guidewire slider, as well as related devices and methods. In some embodiments, a catheter system may include a catheter hub, which may include a distal end and a proximal end. In some embodiments, the catheter system may include a catheter tube extending distally from the distal end of the catheter hub. In some embodiments, the catheter system may include a needle carrier and a needle extending distally from the needle carrier and through the catheter tube. In some embodiments, the catheter system may include a guidewire slider and a guidewire extending distally from the guidewire slider.

In some embodiments, the catheter system may include a safety slider disposed proximal to the guidewire slider and configured to couple to the guidewire slider in response to proximal sliding of the guidewire slider. In some embodiments, in response to the guidewire slider being coupled to the safety slider, the guidewire slider and the safety slider may be configured to slide together from a proximal position to a distal position. In some embodiments, in response to the guidewire slider and the safety slider sliding together from the proximal position to the distal position, the safety slider may be configured to couple to a proximal end of the needle carrier. In some embodiments, the guidewire slider and the safety slider may be configured to return to the proximal position with the needle carrier.

In some embodiments, the catheter system may include a housing, which may include a slot. In some embodiments, the guidewire slider and the safety slider may extend through the slot and may be configured to slide along the slot. In some embodiments, the slot may include a bump. In some embodiments, the safety slider may include another bump. In some embodiments, when the guidewire slider and the safety slider are in the proximal position, the bump of the slot may be distal to and contacting the other bump of the safety slider to provide resistance to distal sliding of the safety slider.

In some embodiments, the safety slider may include a first arm and a second arm opposite the firm arm. In some embodiments, a distal end of the first arm may include a first hook feature. In some embodiments, a distal end of the second arm may include a second hook feature. In some embodiments, the proximal end of the needle carrier may include a first flange and a second flange. In some embodiments, in response to the guidewire slider and the safety slider sliding together from the proximal position to the distal position, the first hook and the second hook may be configured to couple to the first flange and the second flange, respectively, to couple the safety slider to the proximal end of the needle carrier.

In some embodiments, the safety slider may include the first arm, the second arm opposite the firm arm, and a boss in between the first arm and the second arm. In some embodiments, an upper surface of the guidewire slider may include a groove. In some embodiments, when the safety slider is coupled to the guidewire slider, the boss feature may sit within the groove.

In some embodiments, the safety slider may include the first arm and the second arm opposite the firm arm, and the first arm may include a first snap feature and the second arm may include a second snap feature. In some embodiments, the guidewire slider may include a first corresponding snap feature and a second corresponding snap feature. In some embodiments, the first snap feature and the second snap feature may be configured to snap past the first corresponding snap feature and the second corresponding snap feature, respectively, to couple the safety slider with the guidewire slider in response to the proximal sliding of the guidewire slider.

In some embodiments, an internal surface of the first arm may include the first snap feature and an internal surface of the second arm may include the second snap feature. In some embodiments, a first side of the guidewire slider may include the first corresponding snap feature and a second side of the guidewire slider may include the second corresponding snap feature. In some embodiments, a first side of the boss may include the first snap feature and a second side of the boss may include the second snap feature. In some embodiments, a first internal surface of the guidewire slider may include the first corresponding snap feature and a second internal surface of the guidewire slider may include the second corresponding snap feature. In some embodiments, a distal end of the boss may include a shape corresponding to a shape of the guidewire slider between the first corresponding snap feature and the second corresponding snap feature.

Referring now to a second set of embodiments, a catheter system may include a catheter hub, which may include a distal end and a proximal end. In some embodiments, the catheter system may include a catheter tube extending distally from the distal end of the catheter hub. In some embodiments, the catheter system may include a needle carrier. In some embodiments, the catheter system may include a needle extending distally from the needle carrier and through the catheter tube. In some embodiments, the catheter system may include a guidewire slider, and a guidewire extending distally from the guidewire slider. In some embodiments, the guidewire slider may be configured to couple to the needle carrier in response to proximal sliding of the guidewire slider. In some embodiments, in response to the guidewire slider being coupled to the needle carrier, the guidewire slider and the needle carrier may be configured to slide together proximally.

In some embodiments, the guidewire slider may include a living hinge. In some embodiments, an outer surface of the needle carrier may include a groove. In some embodiments, the living hinge may be configured to extend into the groove to couple to the needle carrier in response to proximal sliding of the guidewire slider.

In some embodiments, the guidewire slider may include a snap protrusion. In some embodiments, a proximal end of the needle carrier may include a groove and a bump disposed in the groove. In some embodiments, the snap protrusion may be configured to snap into the groove to couple to the needle carrier in response to distal sliding of the guidewire slider.

In some embodiments, the guidewire slider may include multiple teeth. In some embodiments, a proximal end of the needle carrier may include a bump feature. In some embodiments, the teeth may be configured to catch on the bump feature to couple the guidewire slider to the needle carrier in response to distal sliding of the guidewire slider.

In some embodiments, the needle carrier may include a septum having a groove. In some embodiments, the guidewire slider may include a distally-extending arm having a protrusion, and the protrusion of the distally-extending arm may be configured to fit within the groove of the septum to couple the guidewire slider to the needle carrier in response to distal sliding of the guidewire slider. In some embodiments, the septum may be constructed of plastic.

In some embodiments, an inner surface of a proximal end of the needle carrier may include a snap protrusion. In some embodiments, the guidewire slider may include a distally-extending protrusion having a ridge. In some embodiments, the ridge may be configured to snap onto the snap protrusion to couple the guidewire slider to the needle carrier in response to distal sliding of the guidewire slider.

In some embodiments, a proximal end of the needle carrier may include an aperture. In some embodiments, the guidewire slider may include a distally-extending arm having an annular protrusion. In some embodiments, the annular protrusion may be configured to snap past the aperture having a smaller diameter than an outer diameter of the annular protrusion to couple the guidewire slider to the needle carrier in response to distal sliding of the guidewire slider.

In a third set of embodiments, a catheter system may include a catheter hub, which may include a distal end and a proximal end. In some embodiments, the catheter system may include a catheter tube extending distally from the distal end of the catheter hub. In some embodiments, the catheter system may include a housing coupled to the catheter hub. In some embodiments, the housing may include a first slot and a second slot. In some embodiments, a distal end of the second slot may be proximal to a distal end of the first slot. In some embodiments, a proximal end of the second slot may include a cutout tab.

In some embodiments, the catheter system may include a needle carrier disposed within a lumen of the housing. In some embodiments, the catheter system may include a needle extending distally from the needle carrier and through the catheter tube. In some embodiments, the catheter system may include a guidewire slider configured to slide along the first slot. In some embodiments, the catheter system may include a guidewire extending distally from the guidewire slider.

In some embodiments, the catheter system may include an additional slider configured to slide along the second slot. In some embodiments, the guidewire slider and the additional slider may be coupled together such that the guidewire slider and the additional slider are configured to slide distally together along the first slot and the second slot, respectively. In some embodiments, in response to rotation of the additional slider into the cutout tab, the guidewire slider may be configured to uncouple from the additional slider. In some embodiments, in response to uncoupling the guidewire slider from the additional slider, the guidewire slider may be configured to slide distally independently of the additional slider and couple to the needle carrier. In some embodiments, in response to the guidewire slider being coupled to the needle carrier, the guidewire slider and the needle carrier may be configured to slide together proximally.

In some embodiments, the additional slider may include a protrusion, and the guidewire slider comprises a groove. In some embodiments, in response to rotation of the additional slider into the cutout tab, the protrusion may be configured to remove from the groove to uncouple the guidewire slider from the additional slider. In some embodiments, in response to uncoupling of the guidewire slider from the additional slider, the guidewire slider may be configured to move to a fully advanced position at the distal end of the first slot.

It is to be understood that both the foregoing general description and the following detailed description are examples and explanatory and are not restrictive of the invention, as claimed. It should be understood that the various embodiments are not limited to the arrangements and instrumentality illustrated in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Figure 1A:
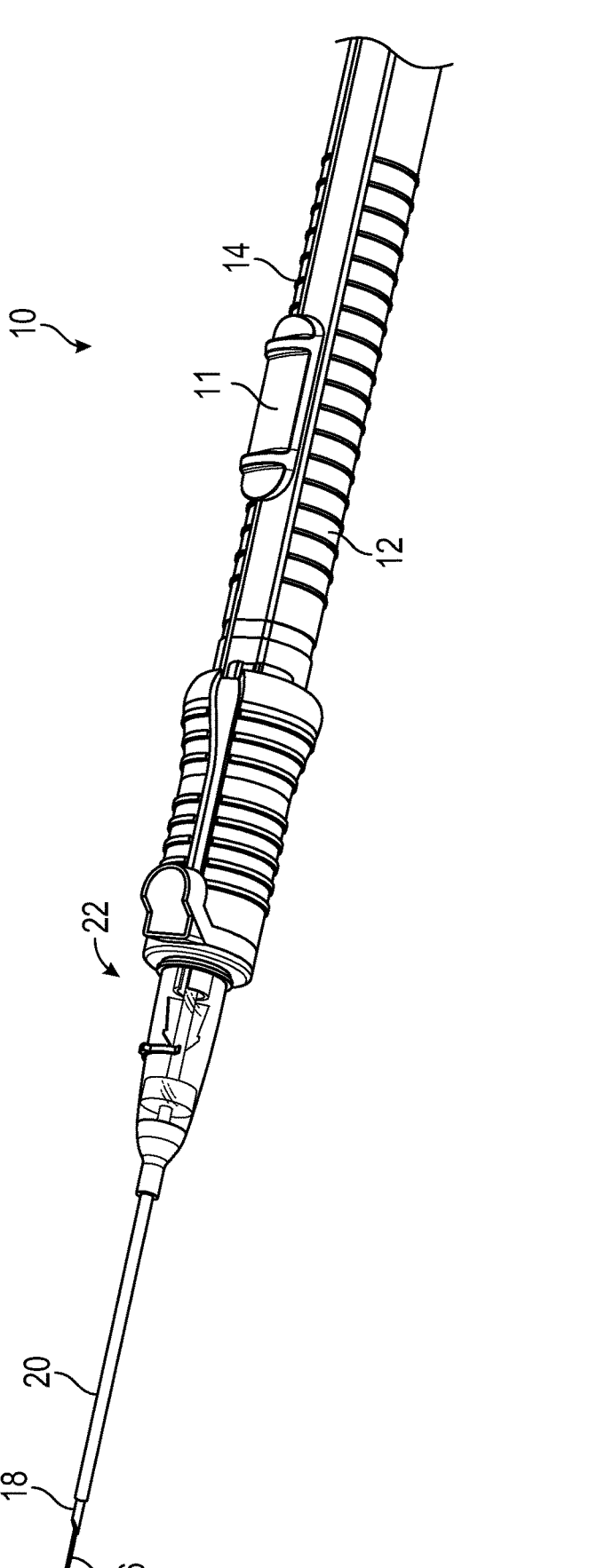
FIG. 1A is an upper perspective view of a prior art catheter system.
Figure 1B:
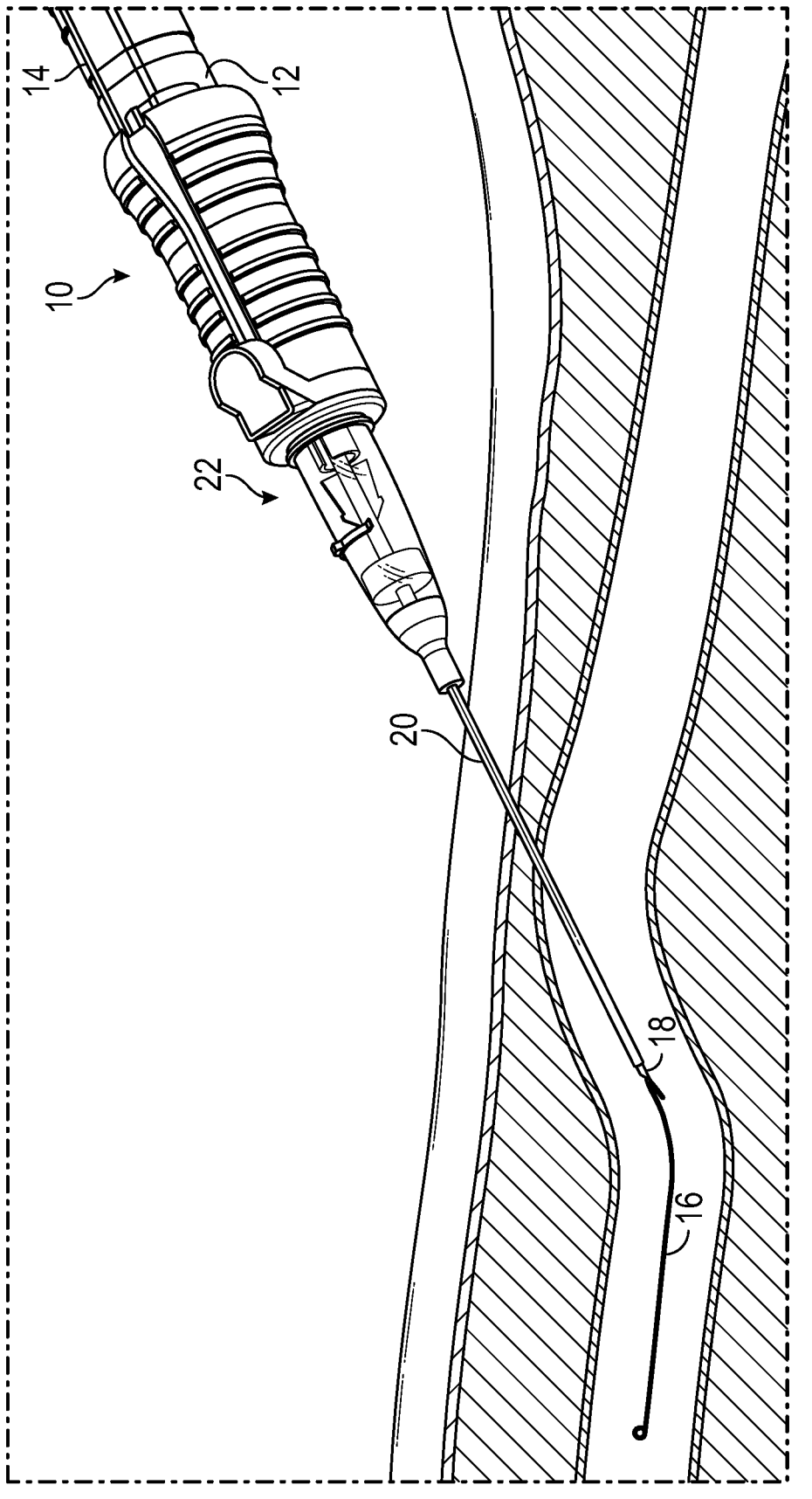
FIG. 1B is an upper perspective view of the prior art catheter system inserted into vasculature of a patient.
Figure 2A:
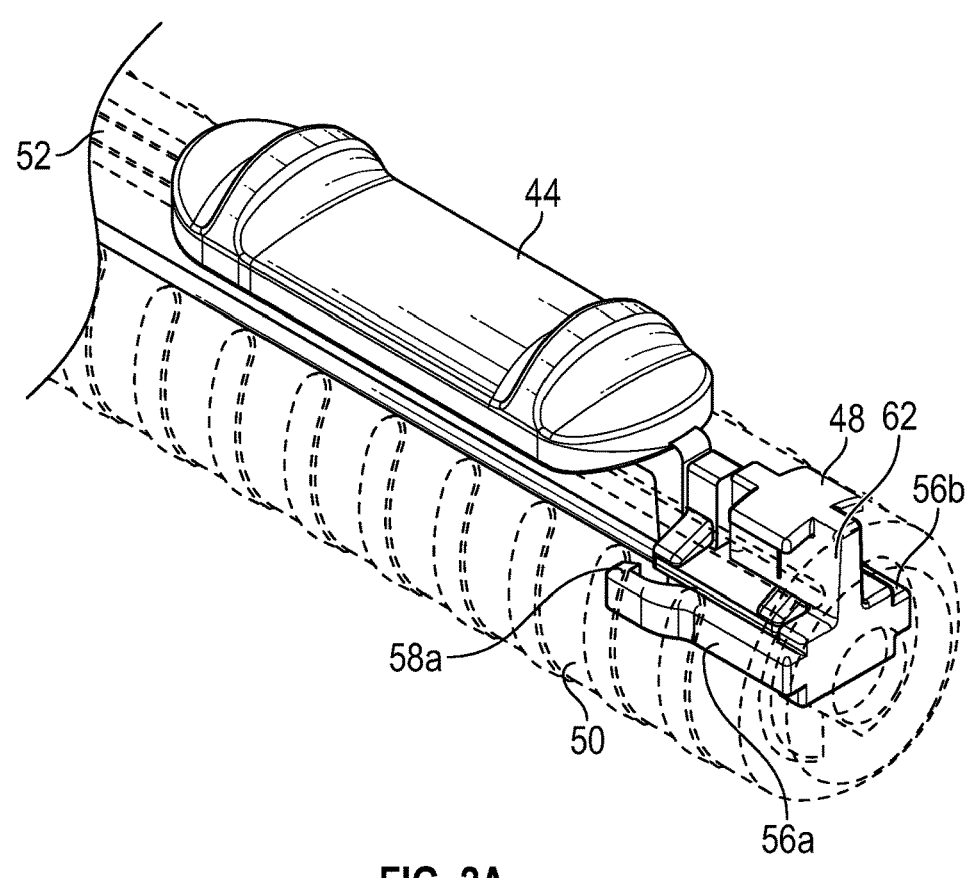
FIG. 2A is an upper perspective view of an example distal end of a catheter system, according to some embodiments.
Figure 2B:
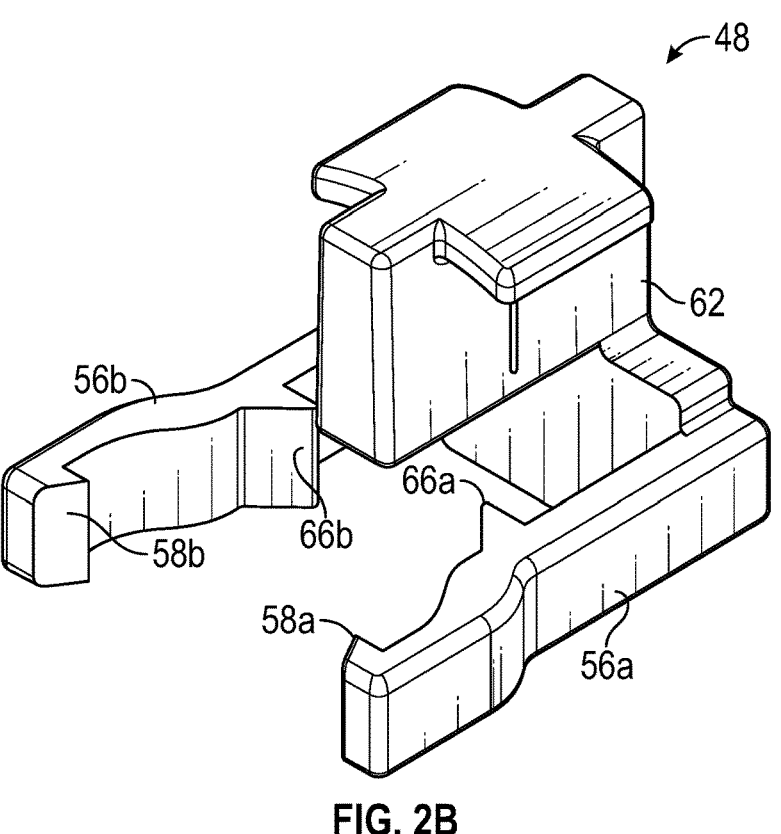
FIG. 2B is an upper perspective view of an example safety slider, according to some embodiments.
Figure 2C:
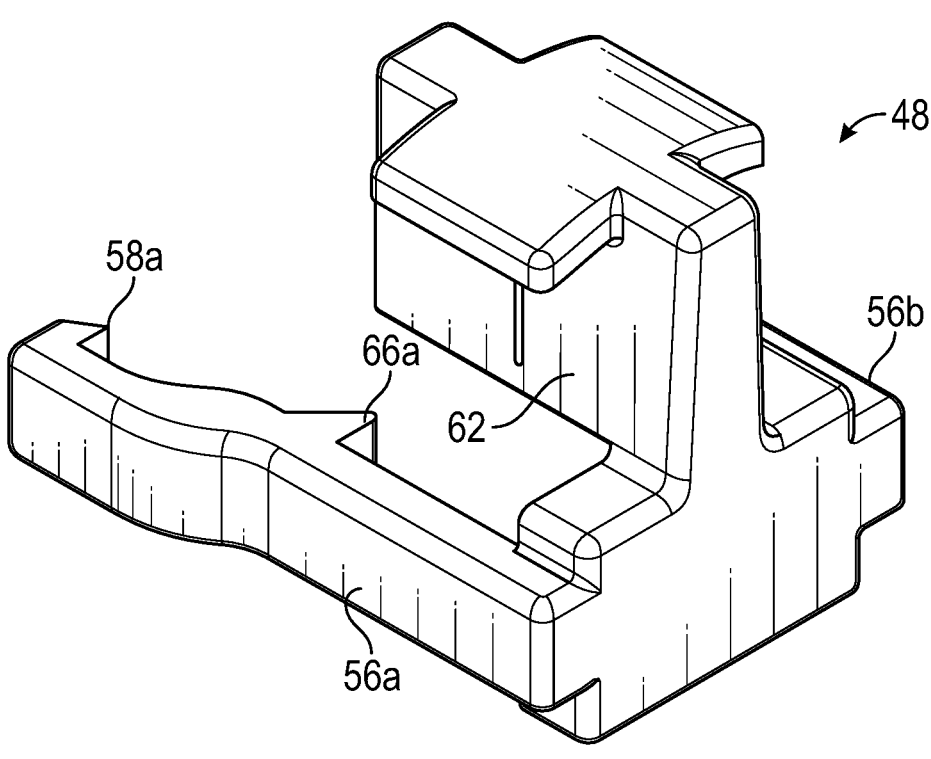
FIG. 2C is another upper perspective view of the safety slider, according to some embodiments.
Figure 2D:
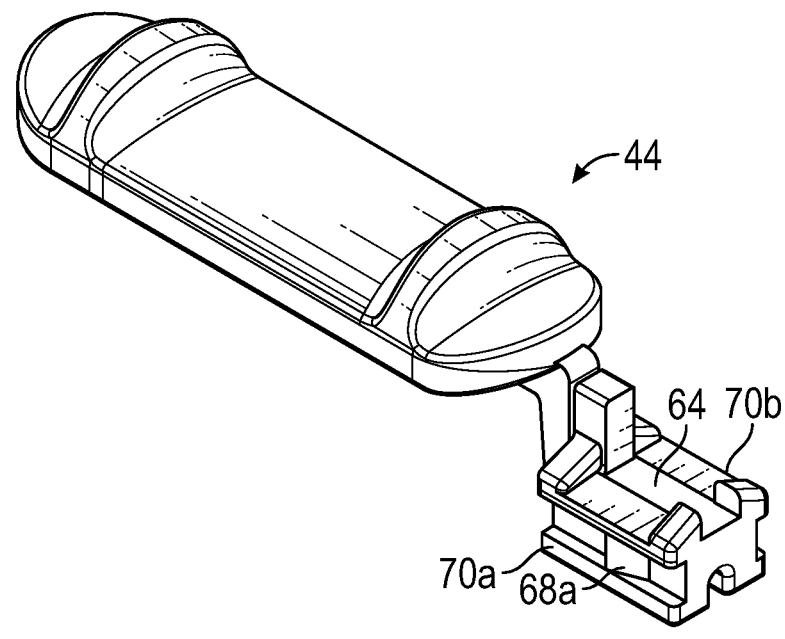
FIG. 2D is an upper perspective view of an example guidewire slider, according to some embodiments.
Figure 2E:
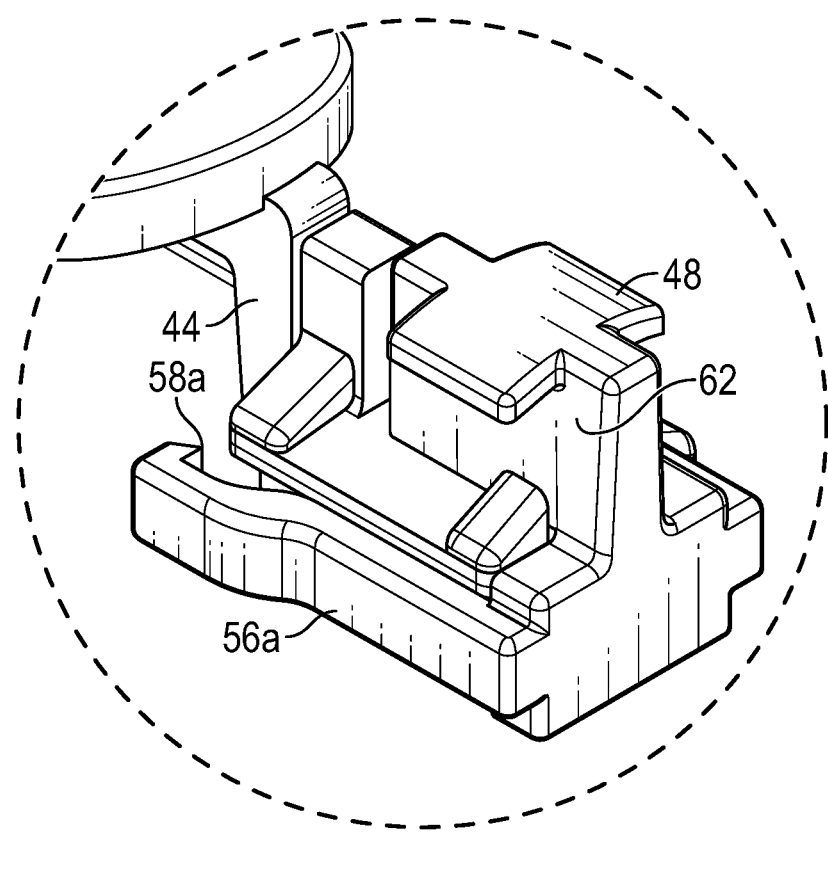
FIG. 2E is an enlarged upper perspective view of the safety slider coupled to the guidewire slider, according to some embodiments.
Figure 2F:
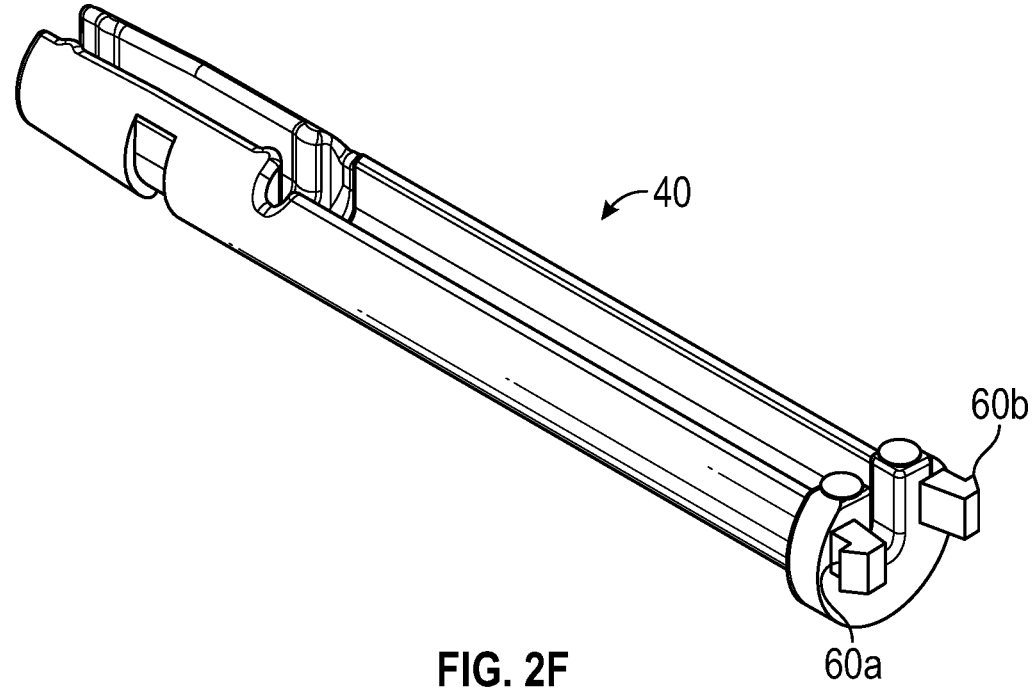
FIG. 2F is an upper perspective view of an example needle carrier, according to some embodiments.
Figure 2G:
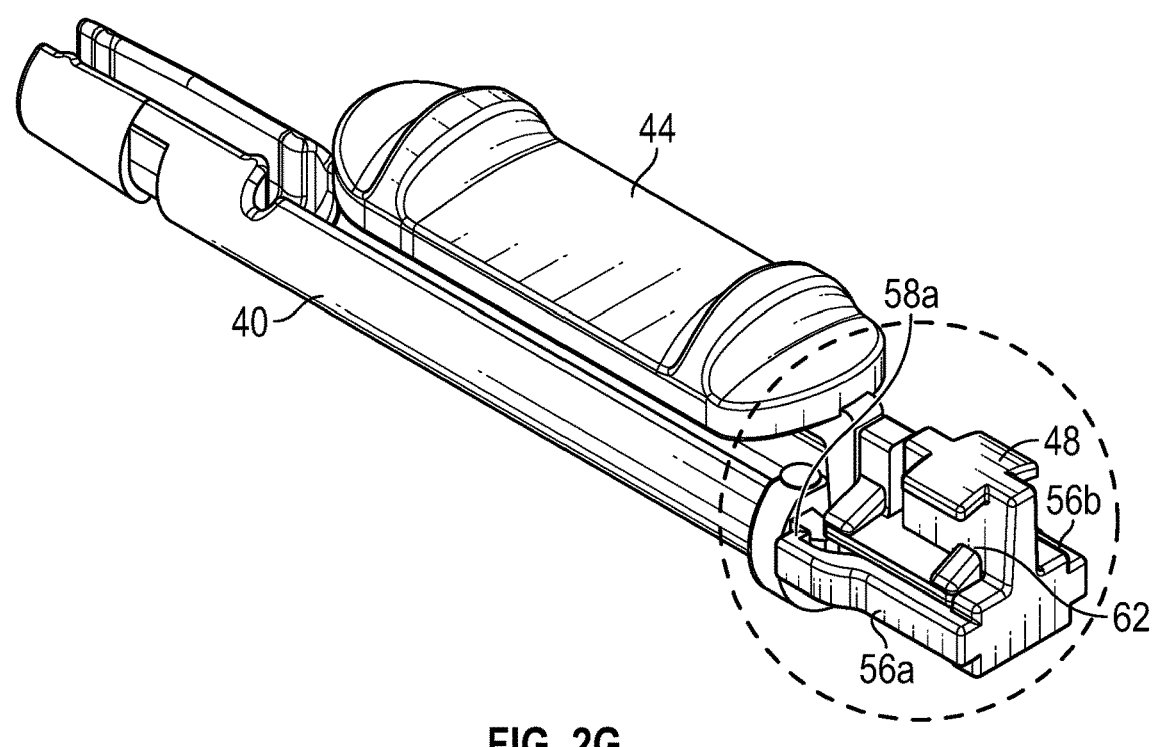
FIG. 2G is an upper perspective view of the needle carrier, the guidewire slider, and the safety slider coupled together, according to some embodiments.
Figure 2H:
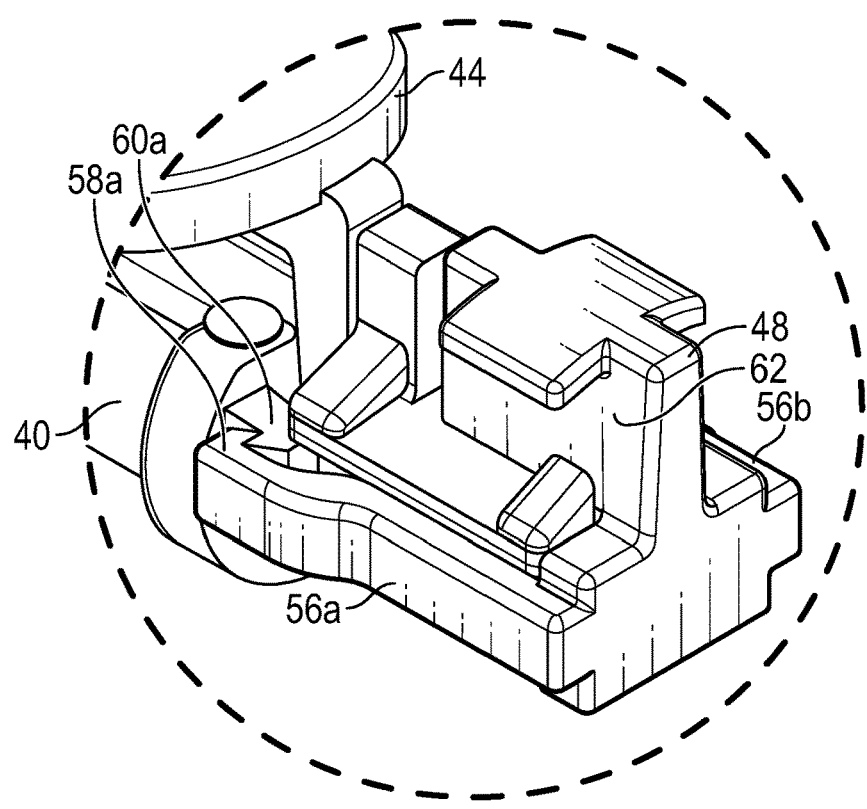
FIG. 2H is an enlarged upper perspective view of a portion of the needle carrier, the guidewire slider, and the safety slider coupled together, according to some embodiments.

As used in the present disclosure, the term "distal" refers to a portion that is described which is further from a clinician, while the term "proximal" refers to a portion that is being described which is closer to the clinician. Referring now to FIGS. 1A-1B, a prior art catheter system 10 is illustrated. The prior art catheter system may correspond to the AccuCath ACE™ Intravascular Catheter, available from Becton, Dickinson & Company of Franklin Lakes, New Jersey, or another catheter system. The prior art catheter system 10 may include a housing 12 and a guidewire slider 11 configured to slide along a slot 14 in the housing 12. The guidewire slider 11 may be coupled to a guidewire 16, which may be configured to advance distally through an introducer needle 18 in response to advancement of the guidewire slider 11. The introducer needle 18 may extend through a catheter 20 of a catheter assembly 22 coupled to the housing 12 to aid in introduction of the catheter 20 into skin and vasculature of a patient.

Advancement of the guidewire 16 distally through the introducer needle 18 may facilitate removal of any obstructions within the vasculature and/or guidance of the catheter 20 into the vasculature. However, if the guidewire 16 is retracted proximally purposefully or accidentally by movement of the guidewire slider 11 when the introducer needle 18 is still extending from the catheter 20, the guidewire 16 may sheared or damaged by the introducer needle 18. An example of this guidewire shearing is illustrated in FIG. 1B. In some cases, if the guidewire 16 is retracted proximally too forcibly through the introducer needle 18 prior to retraction of the introducer needle 18, the guidewire 16 may be sheared completely off by a sharp end of the introducer needle 18 and retained in the patient.

Referring now to FIGS. 2A-3E, in some embodiments, a catheter system 30 may include a catheter hub 32, which may include a distal end 34, a proximal end 36, and a lumen extending through the distal end 34 and the proximal end 36. In some embodiments, the catheter system 30 may include a catheter tube 38 extending distally from the distal end of the catheter hub 32. In some embodiments, the catheter tube 38 may include a peripheral intravenous catheter, a peripherally-inserted central catheter, or a midline catheter.

In some embodiments, the catheter system 30 may include a needle carrier 40 and a needle 42 extending distally from the needle carrier 40 and through the catheter tube 38 in an insertion configuration ready for insertion into the patient. In some embodiments, the catheter system 30 may include a guidewire slider 44 and a guidewire 46 extending distally from the guidewire slider 44.

In some embodiments, the catheter system 30 may include a safety slider 48 disposed proximal to the guidewire slider 44 and configured to couple to the guidewire slider 44 in response to proximal sliding of the guidewire slider 44. In some embodiments, in response to the guidewire slider 44 being coupled to the safety slider 48, the guidewire slider 44 and the safety slider 48 may be configured to slide together from a proximal position, illustrated, for example, in FIG. 2A, to a distal position. In some embodiments, in response to the guidewire slider 44 and the safety slider 48 sliding together from the proximal position to the distal position, the safety slider 48 may be configured to couple to a proximal end of the needle carrier 40.

In some embodiments, the guidewire slider 44 and the safety slider 48 may be configured to return to the proximal position with and at a same time as the needle carrier 40. In further detail, in some embodiments, coupling of the guidewire slider 44 to the safety slider 48 may prevent proximal sliding of the guidewire slider 44 without the needle carrier 40 and the needle 42 coupled thereto. Thus, the guidewire 46 may be prevented from being retracted proximally when the needle 42 is in the insertion configuration to reduce a risk of shearing the guidewire 46.

In some embodiments, the catheter system 30 may include a housing 50, which may include a slot 52. In some embodiments, the guidewire slider 44 and the safety slider 48 may extend through the slot 52 and may be configured to slide along the slot 52. In some embodiments, the needle 42 may be configured to be withdrawn or retracted proximally into the housing 50 from the insertion configuration via a push-button 54 or another suitable mechanism. An example push button mechanism is described further in U.S. Pat. No. 5,501,675, filed Dec. 27, 1994, entitled "SAFETY CATHETER ASSEMBLY HAVING SAFETY STOP PUSH BUT- TON," which is hereby incorporated by reference in its entirety. In some embodiments, the needle 42, which may include an introducer needle having a sharp distal tip, retracted into the housing 50 may shield the sharp distal tip, preventing the clinician from an accidental needle prick. In some embodiments, in response to depression of the push-button 54, a spring may be released and may expand to move the needle carrier 40 proximally with the guidewire slider 44 and the safety slider 48 coupled to the needle carrier 40.

In some embodiments, the safety slider 48 may include a first arm 56a and a second arm 56b opposite the first arm 56a. In some embodiments, a distal end of the first arm 56a may include a first hook feature 58a. In some embodiments, a distal end of the second arm 56b may include a second hook feature 58b. In some embodiments, the proximal end of the needle carrier 40 may include a first flange 60a and a second flange 60b. In some embodiments, in response to the guidewire slider 44 and the safety slider 48 sliding together from the proximal position to the distal position, the first hook feature 58a and the second hook feature 58b may be configured to couple to the first flange 60a and the second flange 60b, respectively, to couple the safety slider 48 to the proximal end of the needle carrier 40. In some embodiments, the first flange 60a and the second flange 60b may each be disposed on an arm configured to provide some flex to facilitate coupling with the first arm 56a and the second arm 56b, which may also be configured to provide some flex to facilitate the coupling.

In some embodiments, the safety slider 48 may include a boss 62, which may include a distally-extending protrusion, in between the first arm 56a and the second arm 56b. In some embodiments, an upper surface of the guidewire slider 44 may include a groove 64. In some embodiments, when the safety slider 48 is coupled to the guidewire slider 44, the boss 62 may sit within the groove 64, which may stabilize the safety slider 48 with respect to the guidewire slider 44.

In some embodiments, the first arm 56a may include a first snap feature 66a and the second arm 56b may include a second snap feature 66b. In some embodiments, the guidewire slider 44 may include a first corresponding snap feature 68a and a second corresponding snap feature. In some embodiments, the first snap feature 66a and the second snap feature 66b may each include a protrusion, and the first corresponding snap feature 68a and the second corresponding snap feature 68b may each include a protrusion.

In some embodiments, the first snap feature 66a and the second snap feature 66b may be configured to snap past the first corresponding snap feature 68a and the second corresponding snap feature, respectively, to couple the safety slider 48 with the guidewire slider 44 in response to the proximal sliding of the guidewire slider 44. In some embodiments, an internal surface of the first arm 56a may include the first snap feature 66a and an internal surface of the second arm 56b may include the second snap feature 66b. In some embodiments, a first side 70a of the guidewire slider 44 may include the first corresponding snap feature 68a and a second side 70b of the guidewire slider 44 may include the second corresponding snap feature. In some embodiments, the second corresponding snap feature may be similar to the first corresponding snap feature 68a but on an opposite side of the guidewire slider 44. In some embodiments, the first corresponding snap feature 68a and the second corresponding snap feature may each be in a groove of the guidewire slider 44 to facilitate a tight fit with the first arm 56a and the second arm 56b, respectively.

Figures 3A, 3B, 3C:
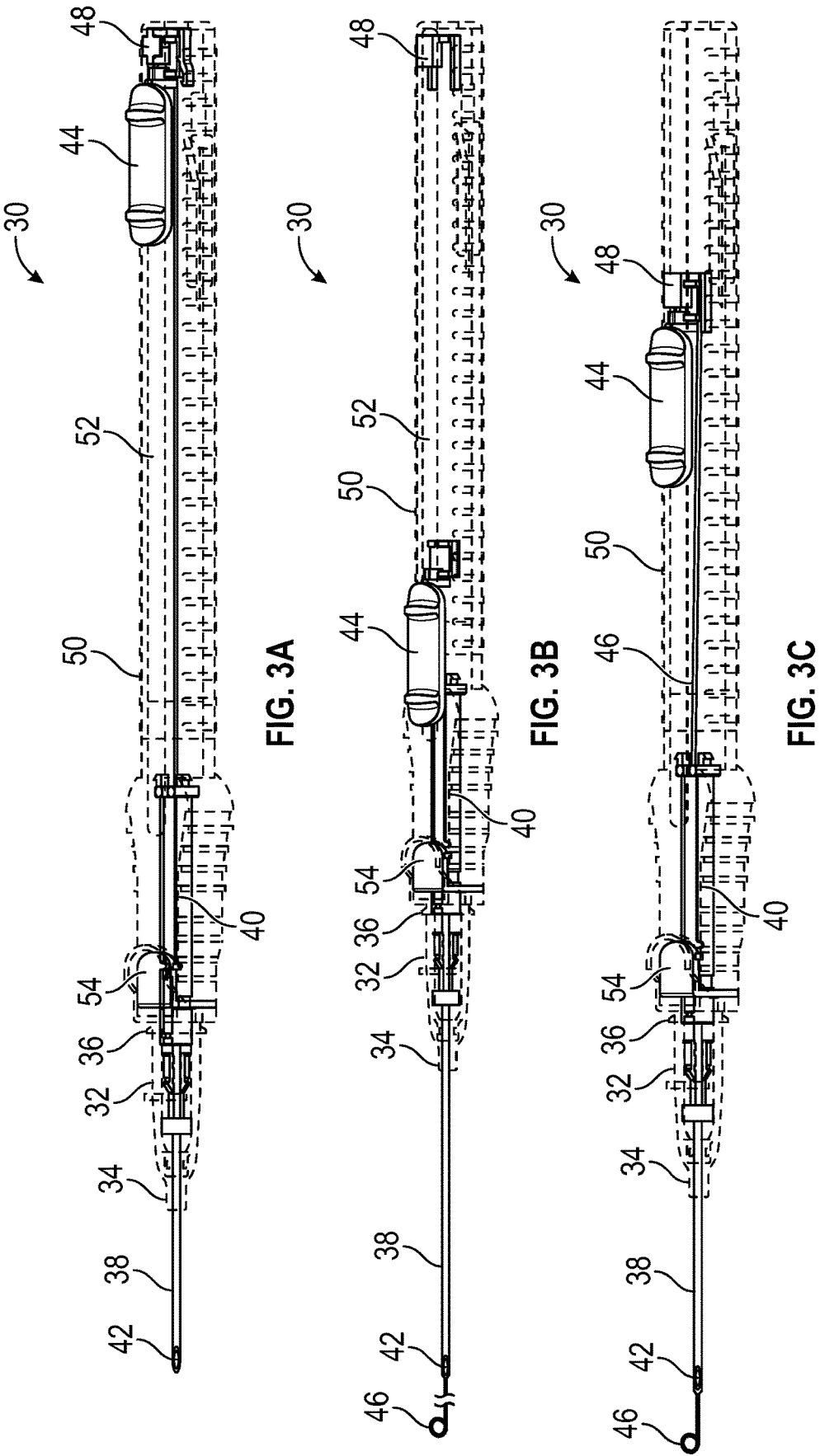
FIG. 3A is an upper perspective view of the catheter system, illustrating the safety slider and the guidewire slider in an initial position, prior to coupling to each other, according to some embodiments.
FIG. 3B is an upper perspective view of the catheter system, illustrating the guidewire slider being tested prior to insertion of the catheter system into the patient, according to some embodiments.
FIG. 3C is an upper perspective view of the catheter system, illustrating the guidewire slider and the safety slider coupled together and advancing distally toward the needle carrier, according to some embodiments.

As illustrated in FIG. 3A, in some embodiments, in an initial position, the guidewire slider 44 may not be coupled to the safety slider 48. As such, the clinician may test the guidewire slider 44 and advancement of the guidewire 46 without risk of coupling to the needle carrier 40. In some instances, the clinician may test the guidewire slider 44 and advancement of the guidewire 46 by sliding the guidewire slider 44 distally, as illustrated in FIG. 3B, and then proximally. In some embodiments, after testing the guidewire 46, the clinician may insert the catheter tube 38 and the needle 42 into the vasculature of the patient.

Figures 3D, 3E, 3F:
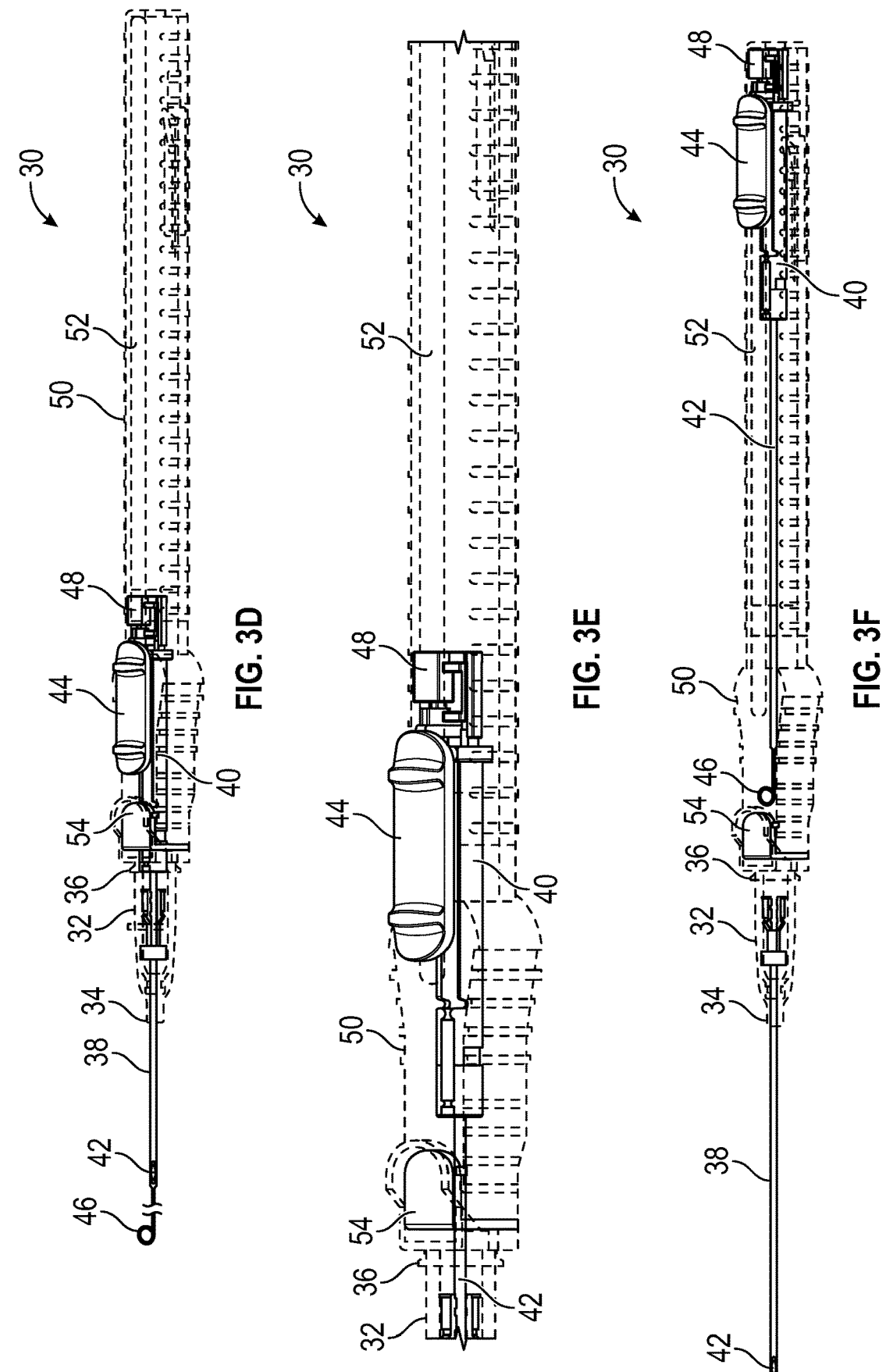
FIG. 3D is an upper perspective view of the catheter system, illustrating the guidewire slider and the safety slider in a distal position and coupled to the needle carrier, according to some embodiments.
FIG. 3E is an upper perspective view of the catheter system, illustrating the guidewire slider, the safety slider, and the needle carrier being slid proximally to enclose the needle within an example housing, according to some embodiments.
FIG. 3F is an upper perspective view of the catheter system, illustrating the guidewire slider and the safety slider in a proximal position, according to some embodiments.

In some embodiments, when the clinician slides the guidewire slider 44 proximally after testing, the clinician may slide the guidewire slider 44 far enough proximally such that the guidewire slider 44 couples to the safety slider 48. In some embodiments, the guidewire slider 44 and the safety slider 48 coupled together may be in the proximal position, ready for simultaneous distal advancement. FIG. 3C illustrates simultaneous distal advancement of the guidewire slider 44 and the safety slider 48 in between the proximal position and the distal position, according to some embodiments. FIG. 3D illustrates the guidewire slider 44 and the safety slider 48 coupled to the needle carrier 40 in the distal position, according to some embodiments.

As illustrated in FIG. 3E, in some embodiments, from the distal position, the guidewire slider 44 and the safety slider 48 may then be slid by the clinician proximally towards the proximal position. It is understood that in some embodiments, the needle 42 may be proximally retracted via an active or passive mechanism. In some embodiments, sliding the guidewire slider 44 and the safety slider 48 proximally may result in proximal movement of the needle carrier coupled to the safety slider 48, thus withdrawing the needle 42 into the housing 50 from the insertion configuration. In other embodiments, the push-button 54 or other active safety mechanism may be activated or pushed, which may result in sliding the guidewire slider 44 and the safety slider 48 proximally towards or into the proximal position, due to pushing by the needle carrier 40.

In some embodiments, in response to the guidewire slider 44 and the safety slider 48 being in the distal position, the guidewire 46 may be fully advanced and disposed beyond a distal end of the catheter tube 38. In some embodiments, in response to the guidewire slider 44 and the safety slider 48 being in the proximal position, the guidewire 46 may be fully retracted and/or entirely disposed within the housing 50, as illustrated, for example, in FIG. 3F.

Figure 4A:
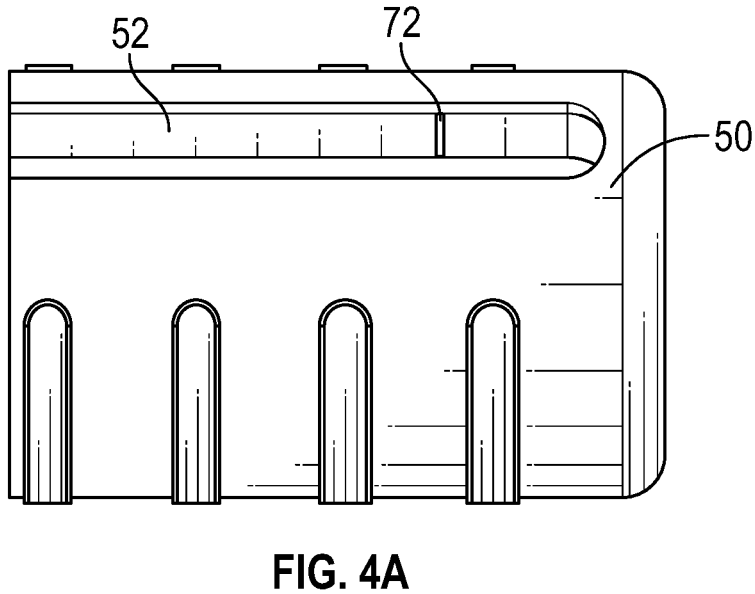
FIG. 4A is an upper perspective view of a portion of the housing, according to some embodiments.
Figure 4B:
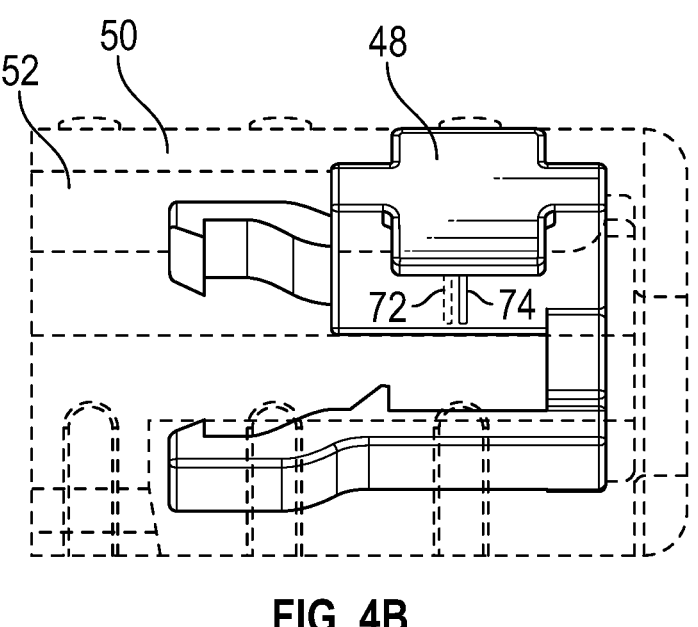
FIG. 4B is an upper perspective view of the safety slider in the initial position, according to some embodiments.

Referring now to FIGS. 4A-4B, in some embodiments, the slot 52 may include a bump 72. In some embodiments, the safety slider 48 may include another bump 74. In some embodiments, when the guidewire slider 44 and the safety slider 48 are in the proximal position, the bump 72 of the slot 52 may be distal to and contacting the other bump 74 of the safety slider 48 to provide resistance to distal sliding of the safety slider 48. In some embodiments, the catheter tube 38 and the needle 42 may be inserted into the vasculature when the guidewire slider 44 and the safety slider 48 are in the proximal position.

Figure 11A:
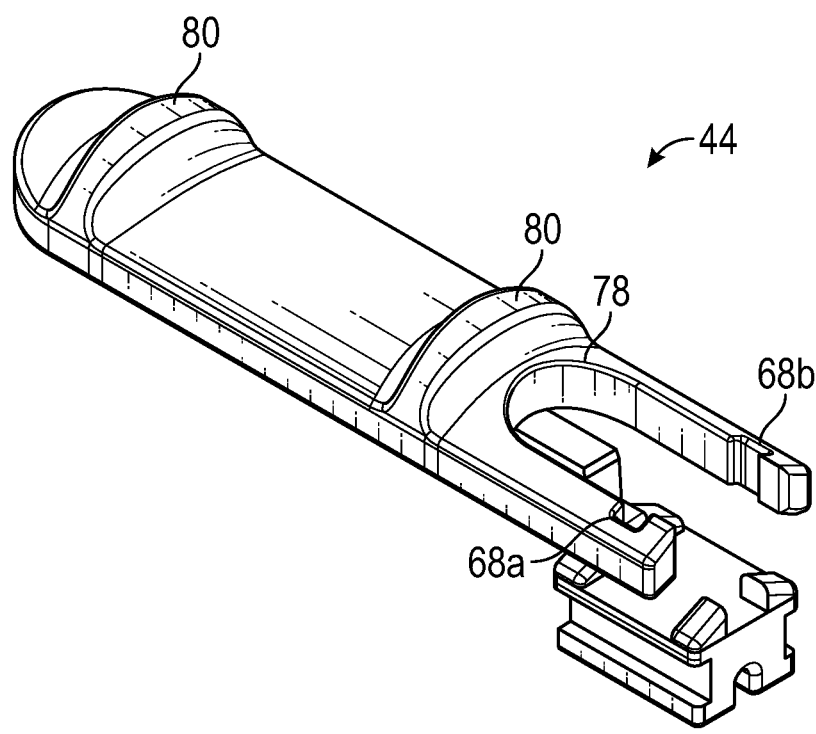
FIG. 11A is an upper perspective view of the guidewire slider, according to some embodiments.
Figure 11B:
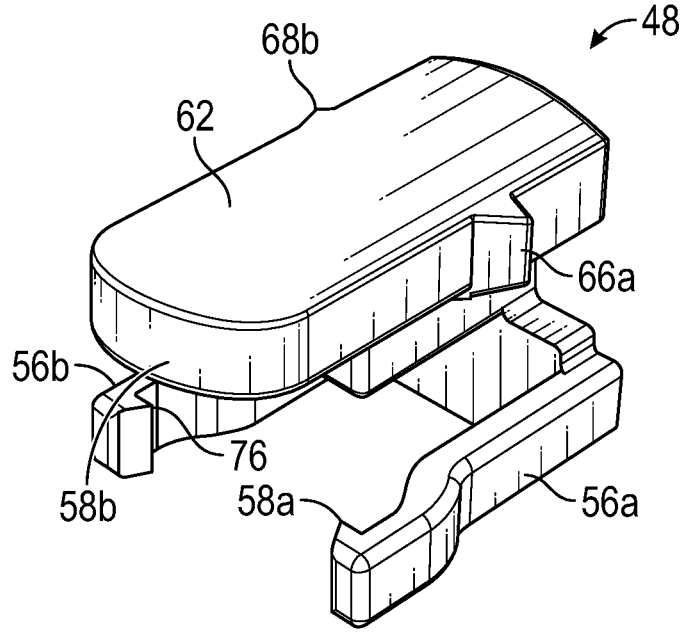
FIG. 11B is an upper perspective view of the safety slider, according to some embodiments.
Figure 12A:
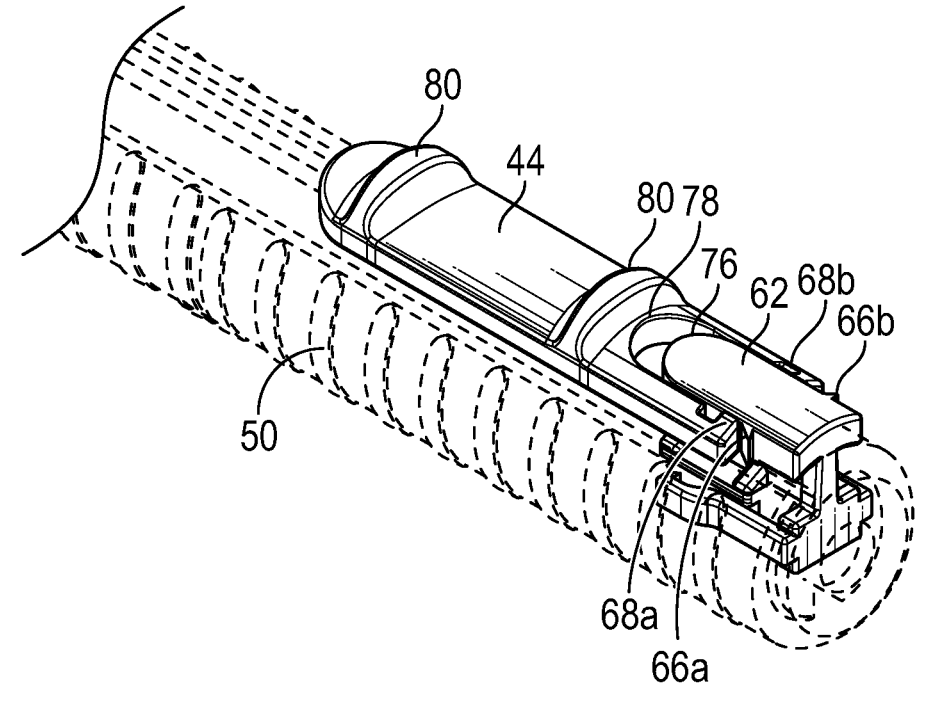
FIG. 12A is an upper perspective view of the safety slider and the guidewire slider in the initial position prior to coupling together, according to some embodiments.
Figure 12B:
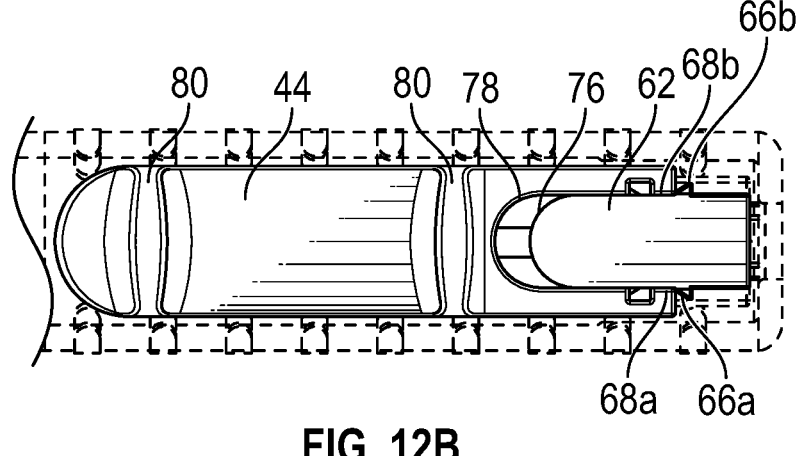
FIG. 12B is a top view of the safety slider and the guidewire slider in the initial position prior to coupling together, according to some embodiments.
Figure 13A:
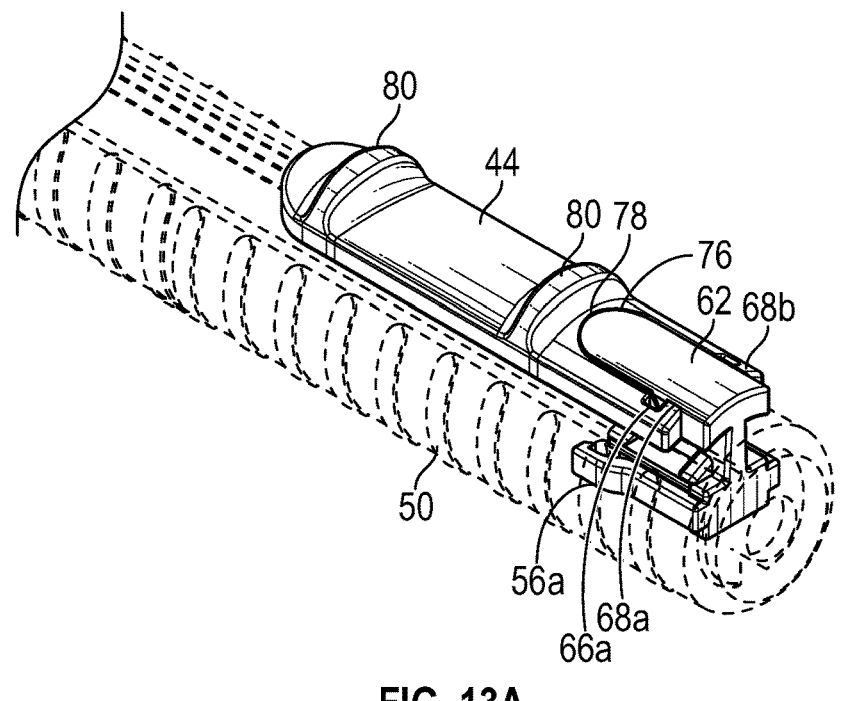
FIG. 13A is an upper perspective view of the safety slider and the guidewire slider coupled together, according to some embodiments.
Figure 13B:
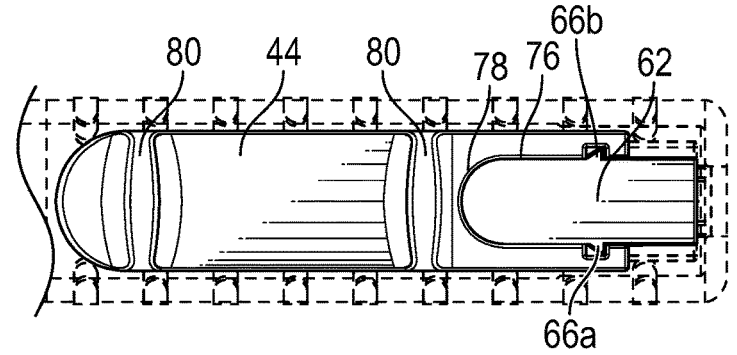
FIG. 13B is a top view of the safety slider and the guidewire slider coupled together, according to some embodiments.
Figure 13C:
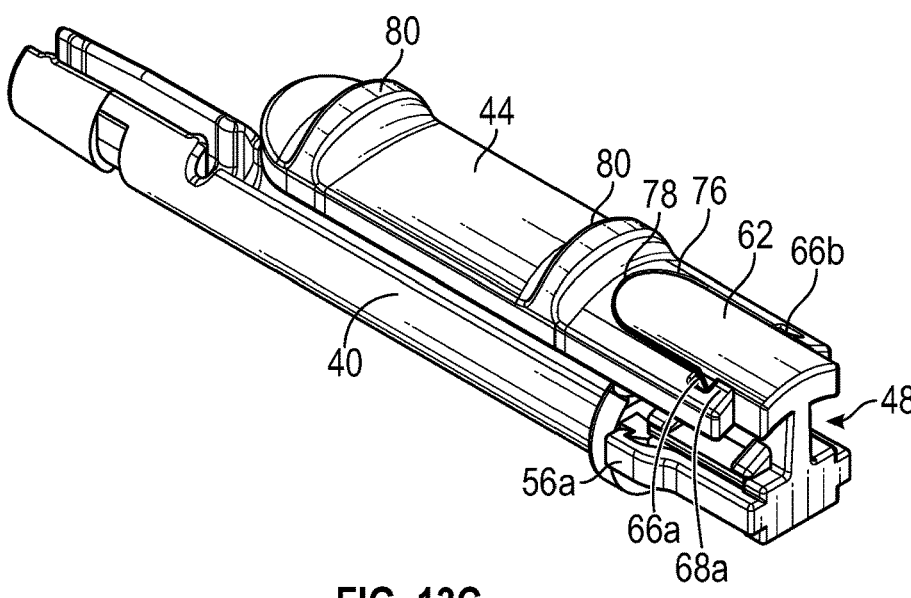
FIG. 13C is an upper perspective view of the safety slider and the guidewire slider coupled together and to the needle carrier, according to some embodiments.

Referring now to FIGS. 11-13, in some embodiments, a first side of the boss 62 may include the first snap feature 66a and a second side of the boss 62 may include the second snap feature 66b. In some embodiments, a first internal surface of the guidewire slider 44 may include the first corresponding snap feature 68a and a second internal surface of the guidewire slider 44 may include the second corresponding snap feature 68b. In some embodiments, the first snap feature 66a, the second snap feature 66b, the first corresponding snap feature 68a, and the second corresponding snap feature 68b may be disposed outside the housing 50. In some embodiments, the first snap feature 66a and the second snap feature 66b may each include a protrusion, and the first corresponding snap feature 68a and the second corresponding snap feature 68b may each include a protrusion, which may each be proximate a groove configured to receive the first snap feature 66a or the second snap feature 66b.

In some embodiments, a distal end of the boss 62 may include a shape 76 corresponding to a shape 78 of the guidewire slider 44 between the first corresponding snap feature 68a and the second corresponding snap feature 68b. In some embodiments, the shape 76 may correspond to the shape 78 such that the shape 76 fits into the shape 78 and creates a generally smooth, generally flush interface between the guidewire slider 44 and the safety slider 48 to facilitate contact with a finger of the clinician. In some embodiments, an upper surface of the guidewire slider 44 and/or the safety slider 48 may include one or more grip features 80 to facilitate movement of the guidewire slider 44 by the finger of the clinician.

Figure 5A:
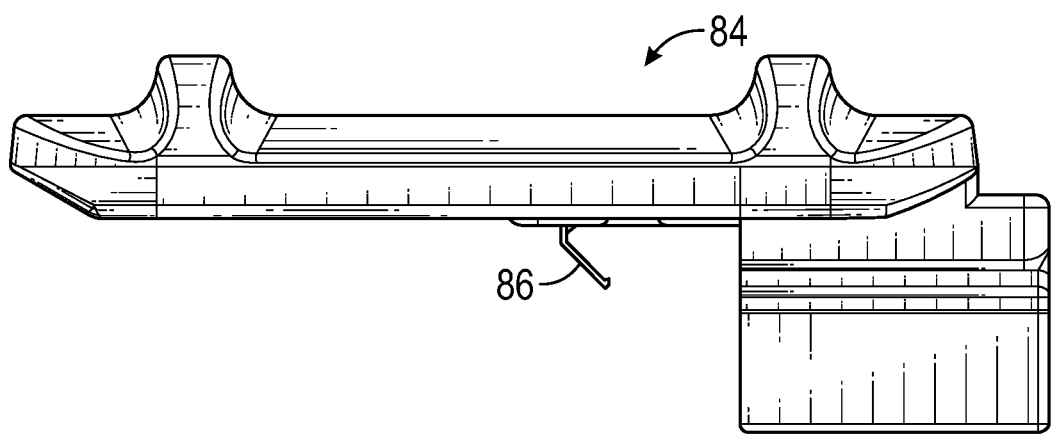
FIG. 5A is a side view of another example guidewire slider, illustrating an example living hinge, according to some embodiments.
Figure 5B:
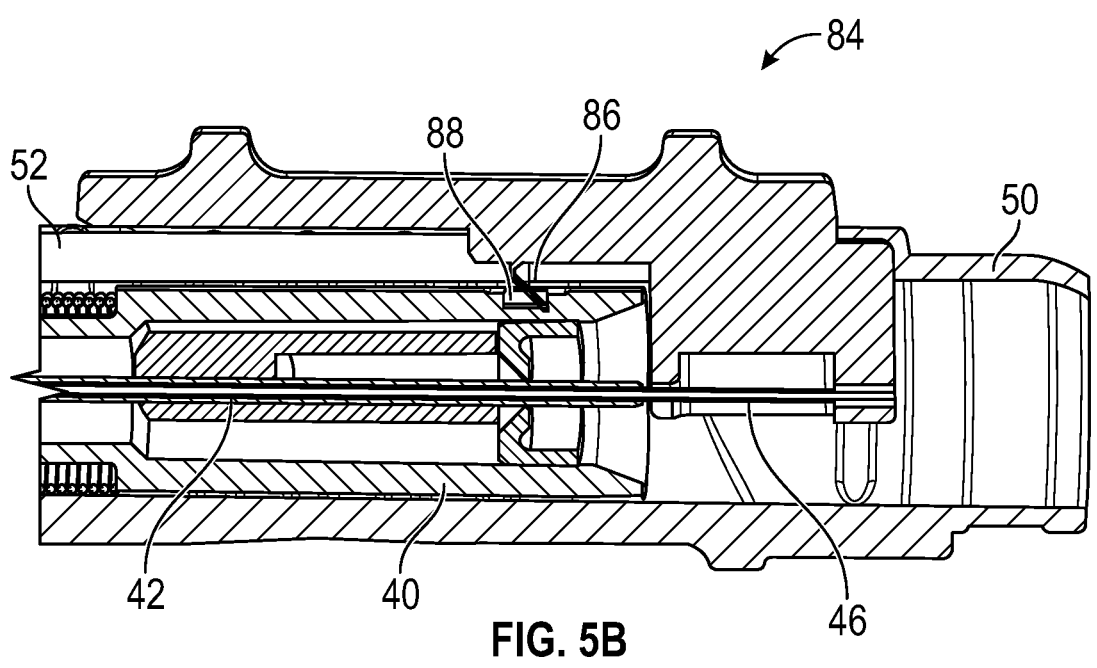
FIG. 5B is a cross-sectional view of the other guidewire slider disposed within the housing in a fully distally advanced position, according to some embodiments.

Referring now to FIGS. 5A-5B, a guidewire slider 84 is illustrated, according to some embodiments. In some embodiments, the guidewire slider 84 may be used with a catheter system similar or identical to the catheter system of FIGS. 2-4 and 11-13 in terms one or more features and/or operation. In some embodiments, the guidewire slider 84 may be similar or identical to the guidewire slider 44 in terms of one or more features and/or operation. In some embodiments, the guidewire slider 84 may be configured to couple to the needle carrier 40 in response to sliding of the guidewire slider 84 within the slot 52. In some embodiments, in response to the guidewire slider 84 being coupled to the needle carrier 40, the guidewire slider 84 and the needle carrier 40 may be configured to slide together proximally.

In some embodiments, the guidewire slider 84 may include a living hinge 86. In some embodiments, an outer surface of the needle carrier 40 may include a groove 88. In some embodiments, the living hinge 86 may be configured to extend into the groove 88 to couple to the needle carrier in response to distal sliding of the guidewire slider 84. In further detail, in some embodiments, the guidewire slider 84 may be configured to couple to the needle carrier 40 in response to distal sliding of the guidewire slider 84 such that the living hinge 86 is aligned with the groove 88 and/or the guidewire slider 84 abuts a proximal end of the needle carrier 40. In some embodiments, even if the clinician tries to slide the guidewire slider 84 proximally, the living hinge 86 within the groove 88 will resist proximal movement of the guidewire slider 84, decreasing a risk of shearing of the guidewire 46 on the needle 42. In some embodiments, the living hinge 86 is bent towards the guidewire slider 84 and points proximally as it moves distally along the needle carrier 40 to the groove 88, and then in response to alignment with the groove 88, the living hinge 86 moves distally and extends into the groove 88.

Figure 6A:
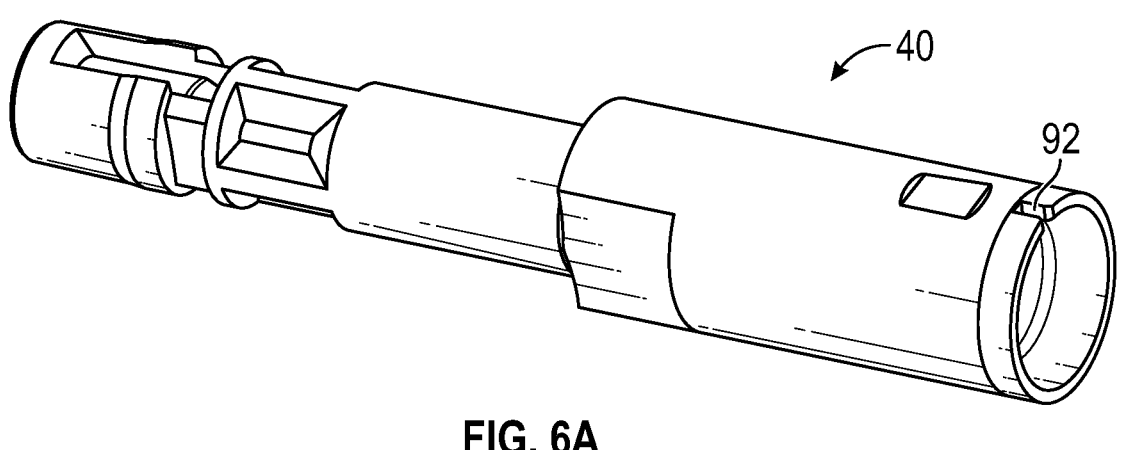
FIG. 6A is an upper perspective view of the needle carrier, according to some embodiments.
Figure 6B:
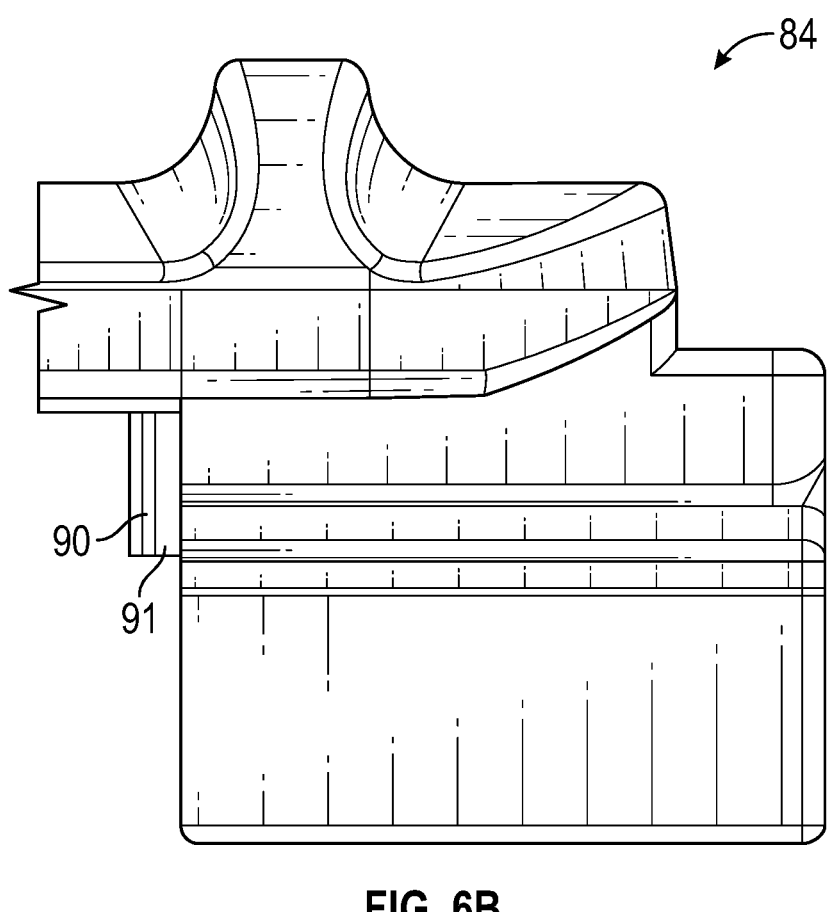
FIG. 6B is a side view of a portion of the other guidewire slider, illustrating an example snap protrusion, according to some embodiments.
Figure 6C:
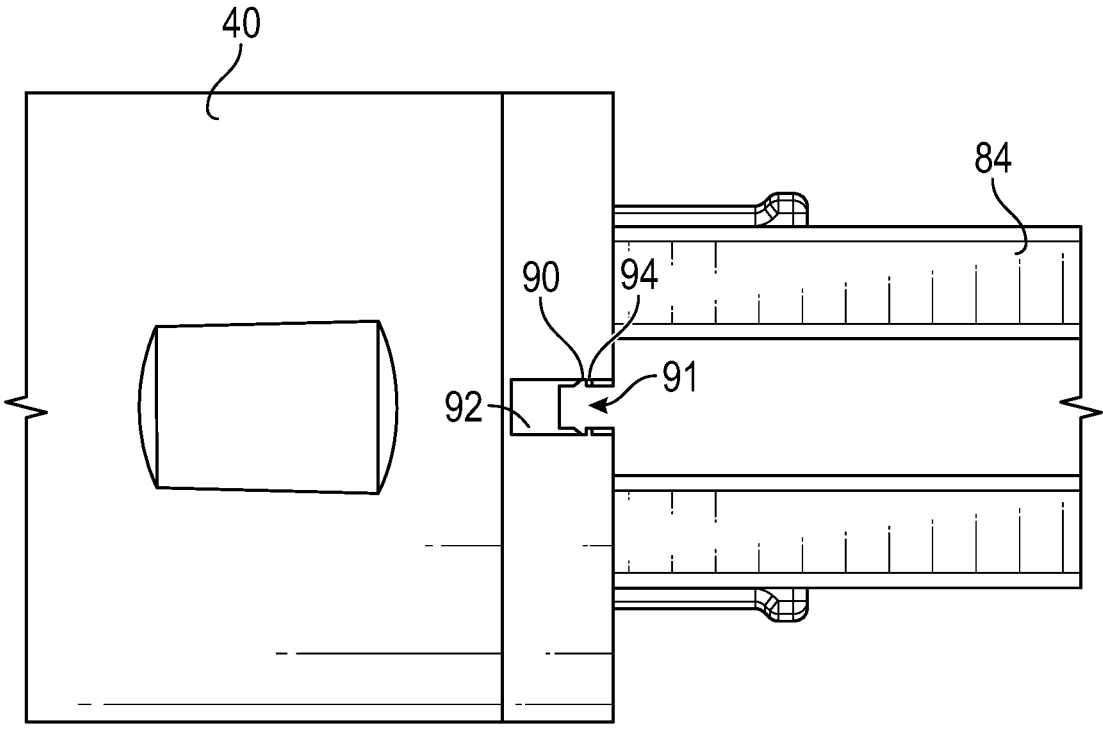
FIG. 6C is a top view of the other guidewire slider, illustrating the snap protrusion inserted into an example groove of the needle carrier, according to some embodiments.

Referring now to FIGS. 6A-6C, in some embodiments, the guidewire slider 84 may include a snap protrusion 90, which may be annular. In some embodiments, the snap protrusion 90 may be disposed on a distally-extending knob 91. In some embodiments, the proximal end of the needle carrier 40 may include a groove 92 and a bump 94 disposed in the groove 92. In some embodiments, the snap protrusion 90 may be configured to snap into the groove 92 to couple to the needle carrier 40 in response to distal sliding of the guidewire slider 84. In some embodiments, even if the clinician tries to slide the guidewire slider 84 proximally, the coupling between the snap protrusion 90 and the bump 94 will resist proximal movement of the guidewire slider 84 until the push-button is pressed releasing the needle 42, decreasing a risk of shearing of the guidewire 46 on the needle 42.

Figure 7A:
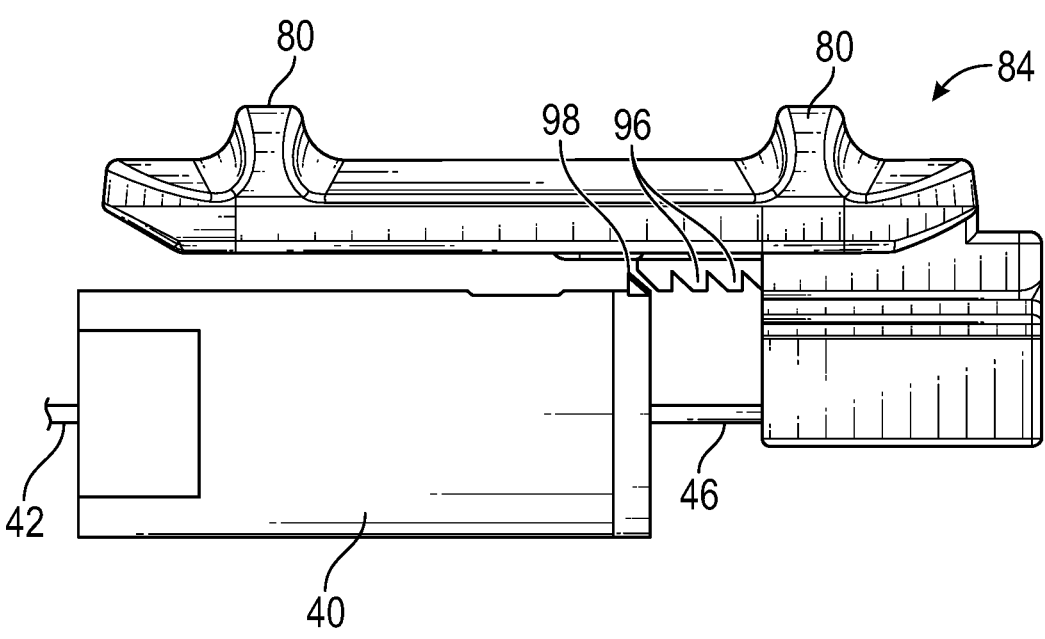
FIG. 7A is a side view of the other guidewire slider, illustrating example teeth, according to some embodiments.
Figure 7B:
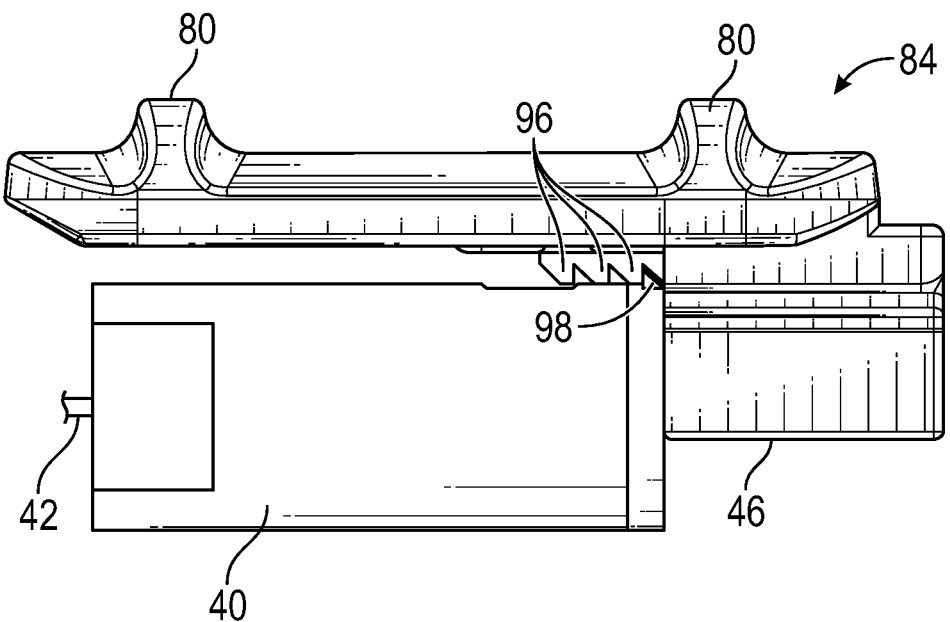
FIG. 7B is a side view of the needle carrier coupled to the other guidewire slider via the teeth, according to some embodiments.
Figure 7C:
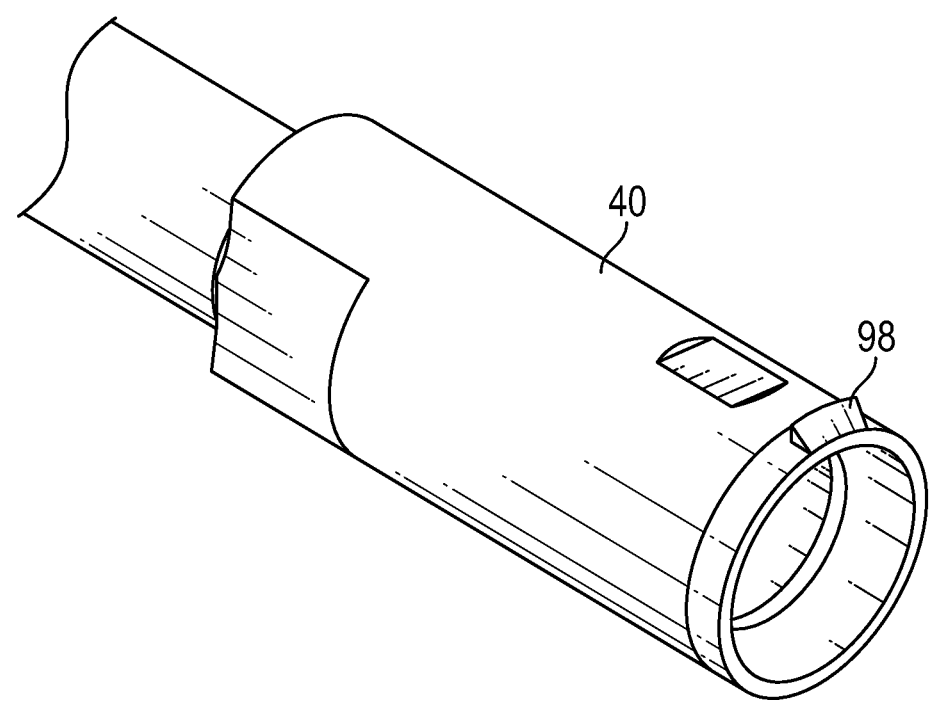
FIG. 7C is an upper perspective view of the needle carrier, according to some embodiments.
Figure 7D:
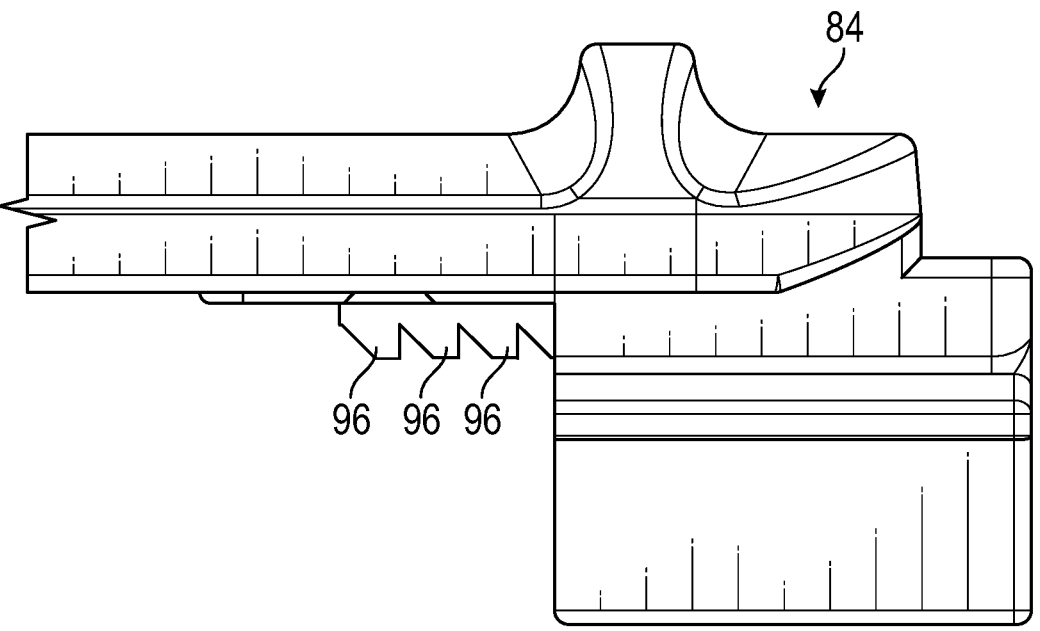
FIG. 7D is a side view of the other guidewire slider, illustrating the teeth, according to some embodiments.

Referring now to FIGS. 7A-7B, in some embodiments, the guidewire slider 84 may include multiple teeth 96. In some embodiments, the proximal end of the needle carrier 40 may include a bump feature 98, which may include a shape corresponding to a shape of the teeth 96. In some embodiments, the teeth 96 may be configured to catch on the bump feature 98 to couple the guidewire slider 84 to the needle carrier 40 in response to distal sliding of the guidewire slider 84. In some embodiments, even if the clinician tries to slide the guidewire slider 84 proximally, the coupling between the teeth 96 and the bump feature 98 will resist movement of the guidewire slider 84 until the push-button is pressed releasing the needle 42, decreasing a risk of shearing of the guidewire 46 on the needle 42. In some embodiments, the teeth 96 may be disposed on a lower surface of a tab portion of the guidewire slider 84 that may include the grip features 80 and is configured for contact with a finger of the clinician.

Figure 8A:
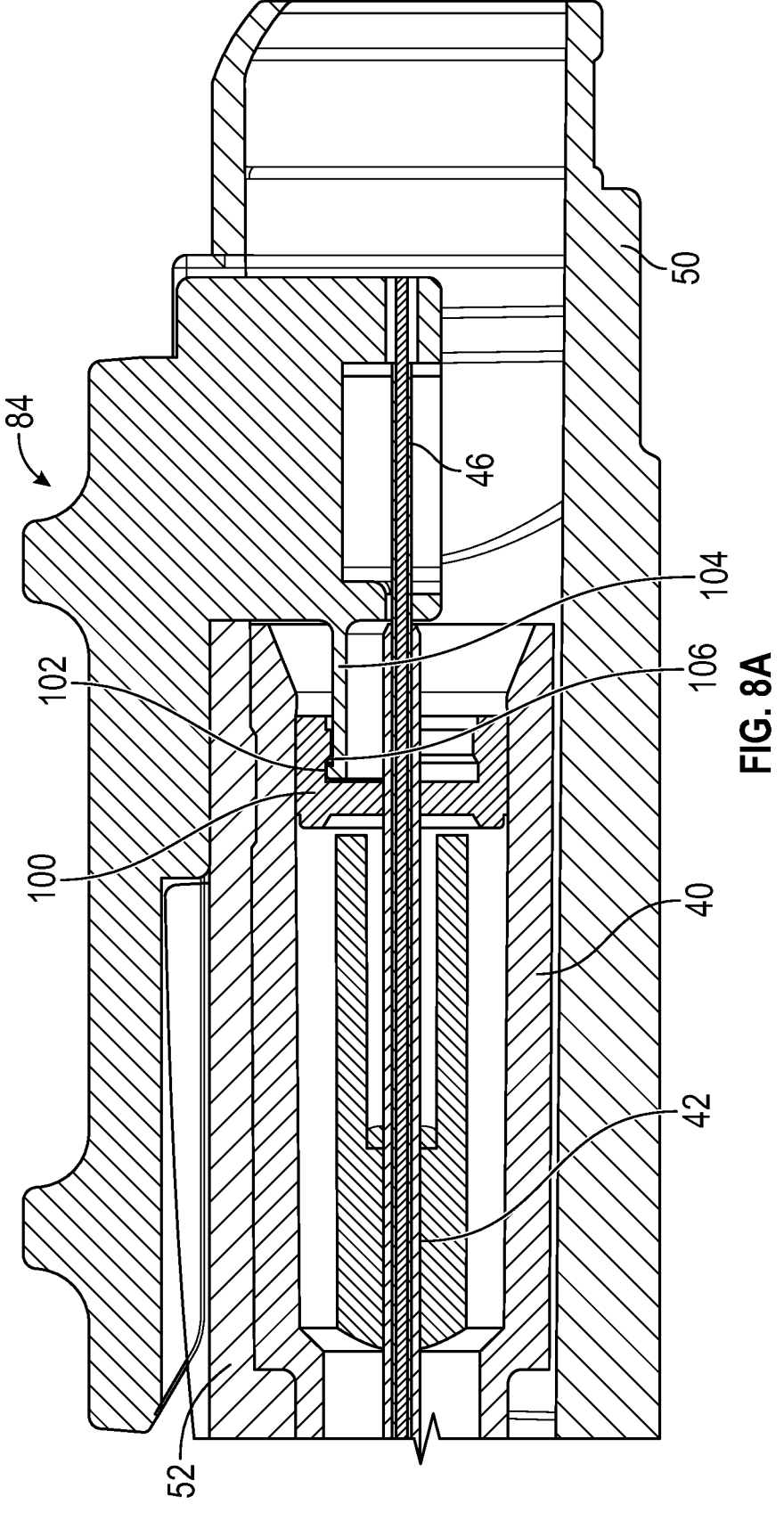
FIG. 8A is a cross-sectional view of the other guidewire slider coupled to an example septum, according to some embodiments.
Figure 8B:
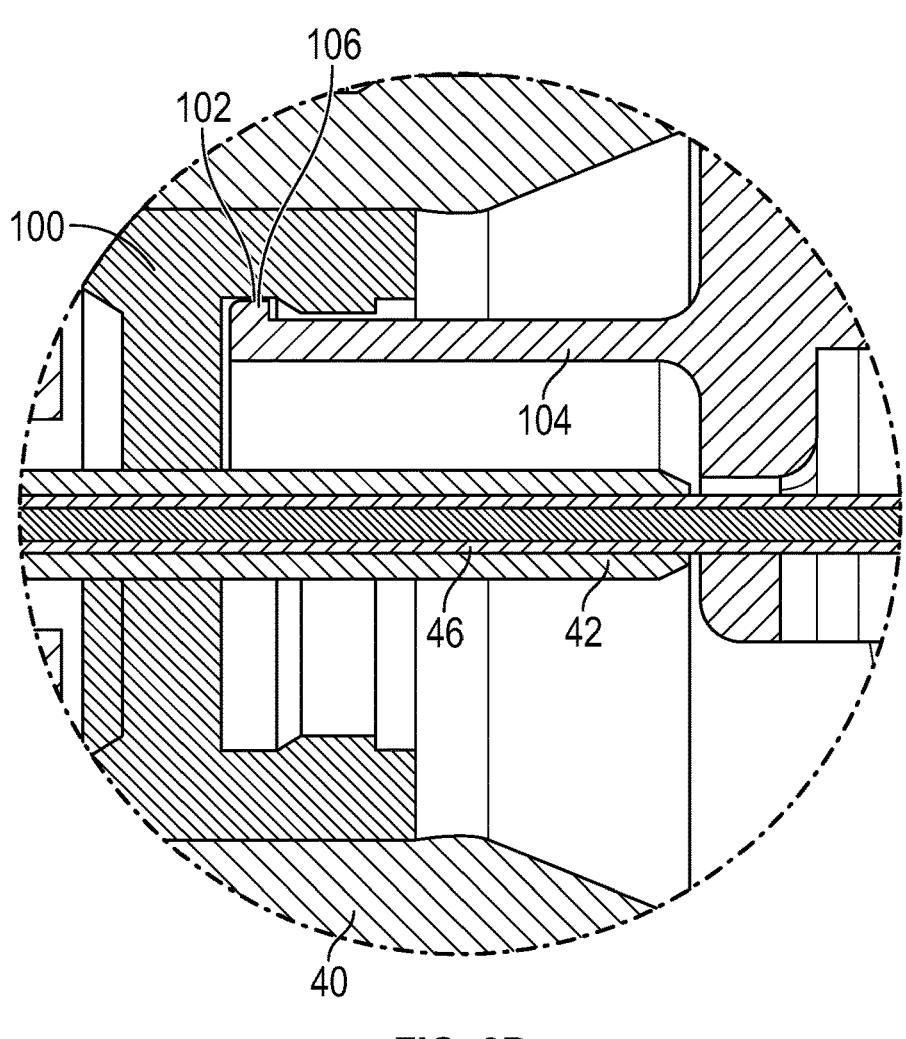
FIG. 8B is an enlarged cross-sectional view illustrating the other guidewire slider coupled to the septum, according to some embodiments.
Figure 8C:
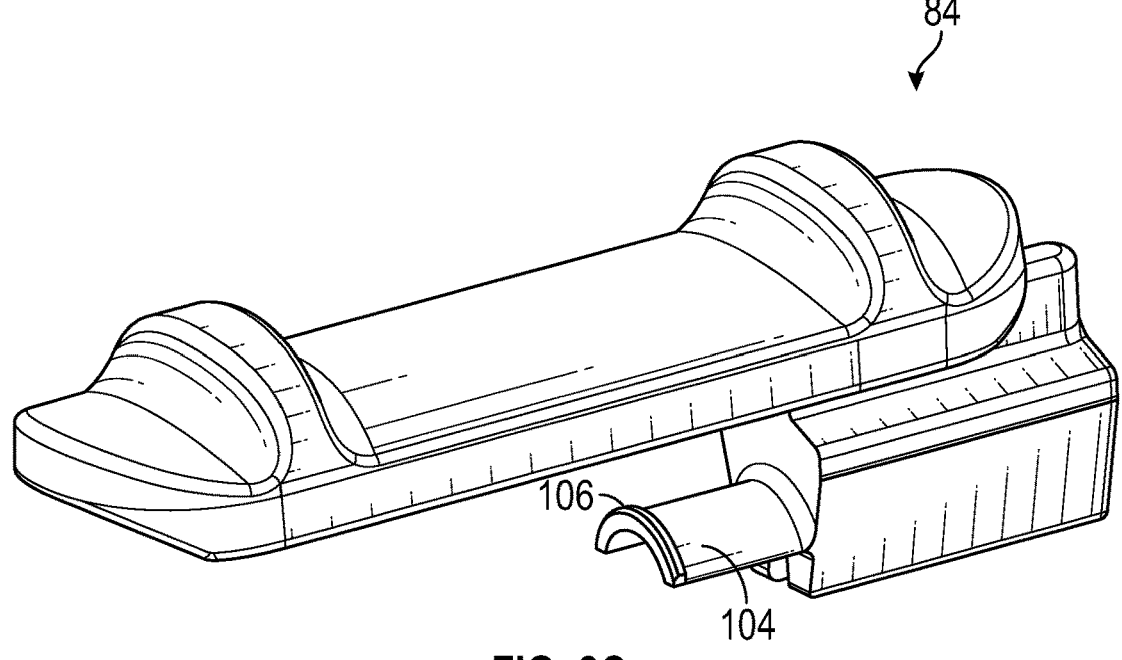
FIG. 8C is an upper perspective view of the other guidewire slider configured to couple to the septum, according to some embodiments.

Referring now to FIGS. 8A-8C, in some embodiments, the needle carrier 40 may include a septum 100 having a groove 102. In some embodiments, the guidewire slider 84 may include a distally-extending arm 104 having a protrusion 106, and the protrusion 106 of the distally-extending arm 104 may be configured to fit within the groove 102 of the septum 100 to couple the guidewire slider 84 to the needle carrier 40 in response to distal sliding of the guidewire slider 84. In some embodiments, the septum 100 may be constructed of plastic, which may facilitate strong coupling between the guidewire slider 84 and the septum 100. In some embodiments, the distally-extending arm 104 and/or the protrusion 106 may be arc-shaped to match a shape of an internal surface of the septum 100 including the groove 102. In some embodiments, even if the clinician tries to slide the guidewire slider 84 proximally, the coupling between the protrusion 106 and the groove 102 will resist movement of the guidewire slider 84 until the push-button is pressed releasing the needle 42, decreasing a risk of shearing of the guidewire 46 on the needle 42.

Figure 9A:
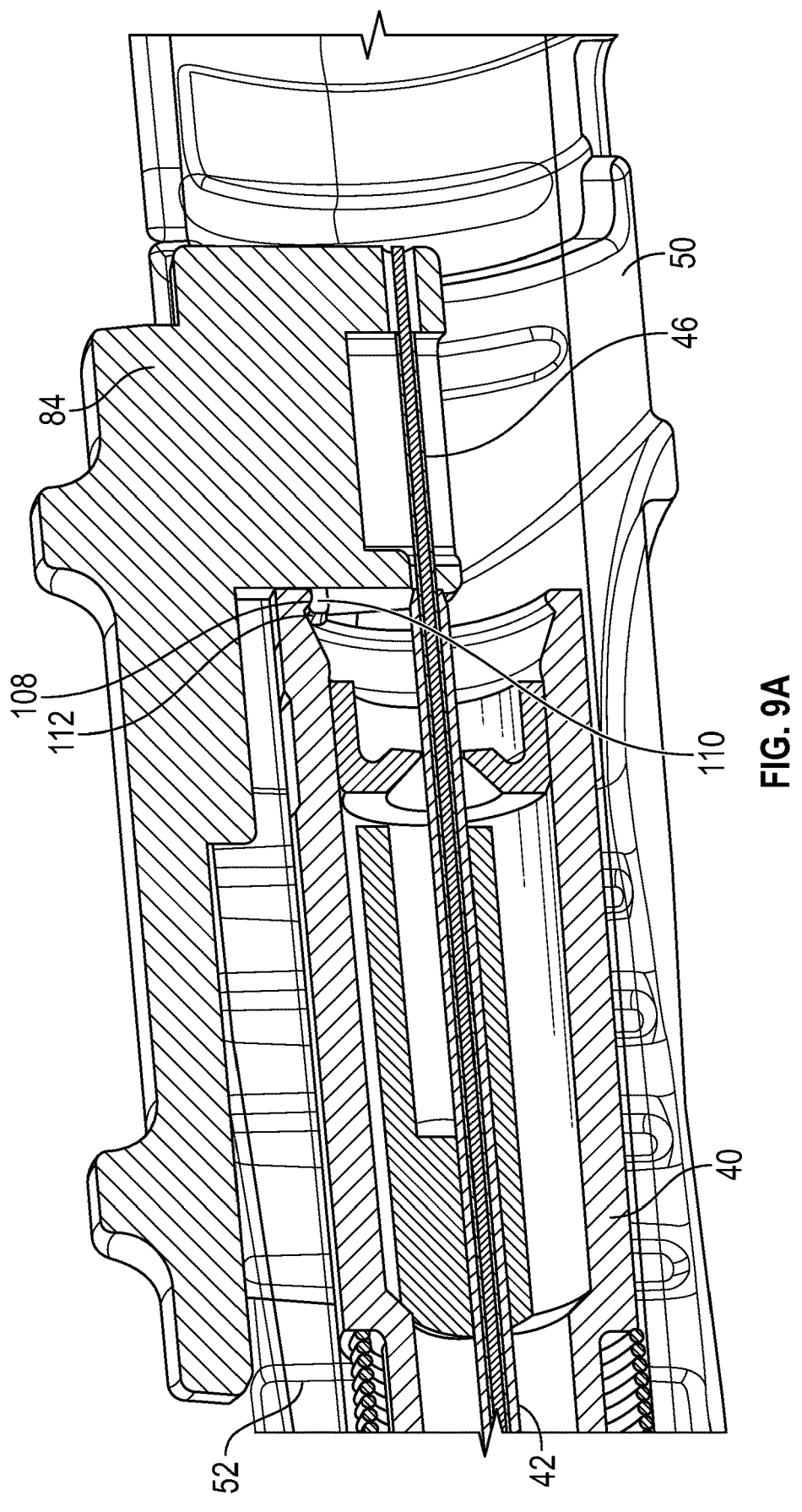
FIG. 9A is a cross-sectional view of the other guidewire slider coupled to the needle carrier, according to some embodiments.
Figure 9B:
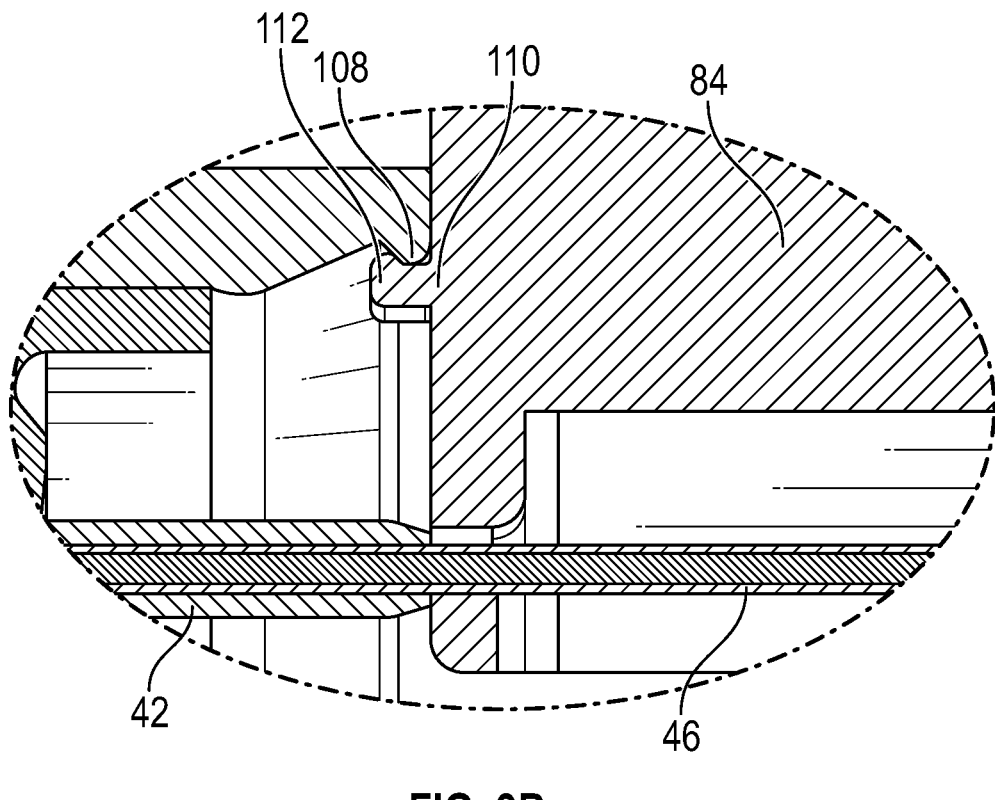
FIG. 9B is an enlarged cross-sectional view illustrating the other guidewire slider coupled to the needle carrier, according to some embodiments.
Figure 9C:
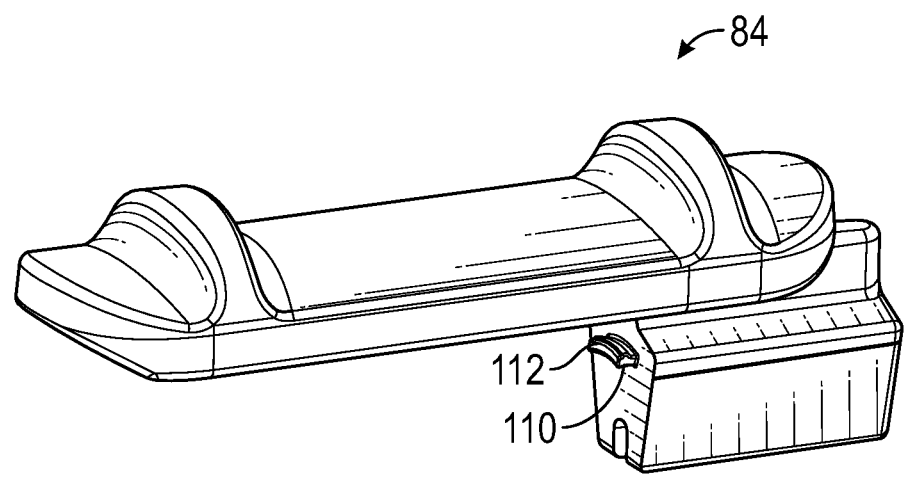
FIG. 9C is an upper perspective view of the other guidewire slider configured to couple to the needle carrier, according to some embodiments.

Referring now to FIGS. 9A-9C, in some embodiments, an inner surface of a proximal end of the needle carrier 40 may include a snap protrusion 108. In some embodiments, the guidewire slider 84 may include a distally-extending protrusion 110 having a ridge 112. In some embodiments, the ridge 112 may be configured to snap onto the snap protrusion 108 to couple the guidewire slider 84 to the needle carrier 40 in response to distal sliding of the guidewire slider 84. In some embodiments, even if the clinician tries to slide the guidewire slider 84 proximally, the contact between the snap protrusion 108 and the ridge 112 will resist movement of the guidewire slider 84 until the push-button is pressed releasing the needle 42, decreasing a risk of shearing of the guidewire 46 on the needle 42.

Figure 10A:
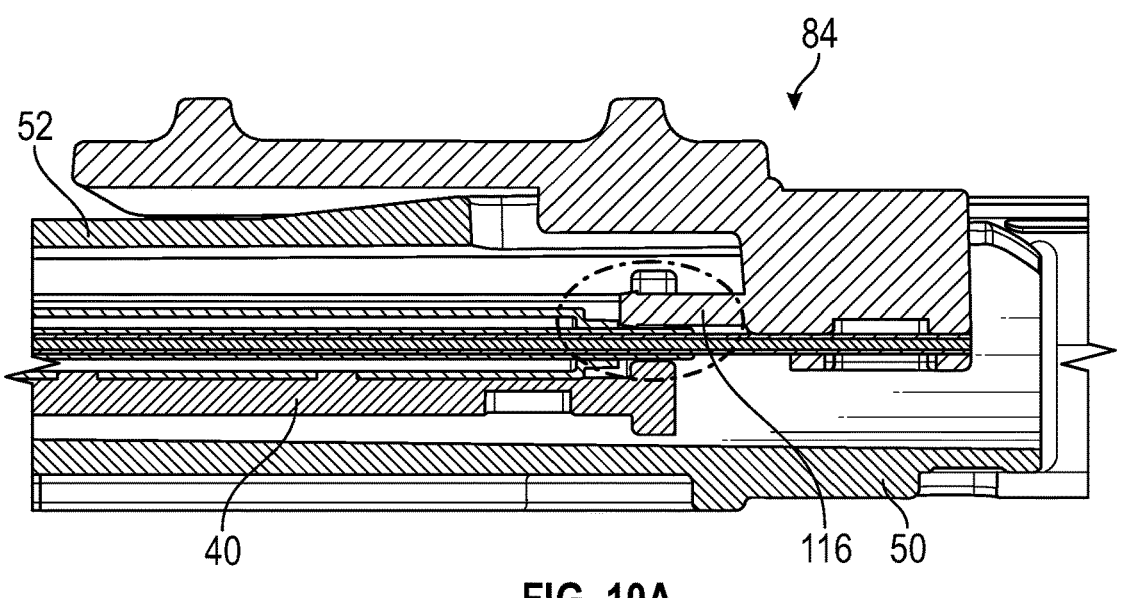
FIG. 10A is a cross-sectional view of the other guidewire slider coupled to the needle carrier via an example aperture, according to some embodiments.
Figure 10B:
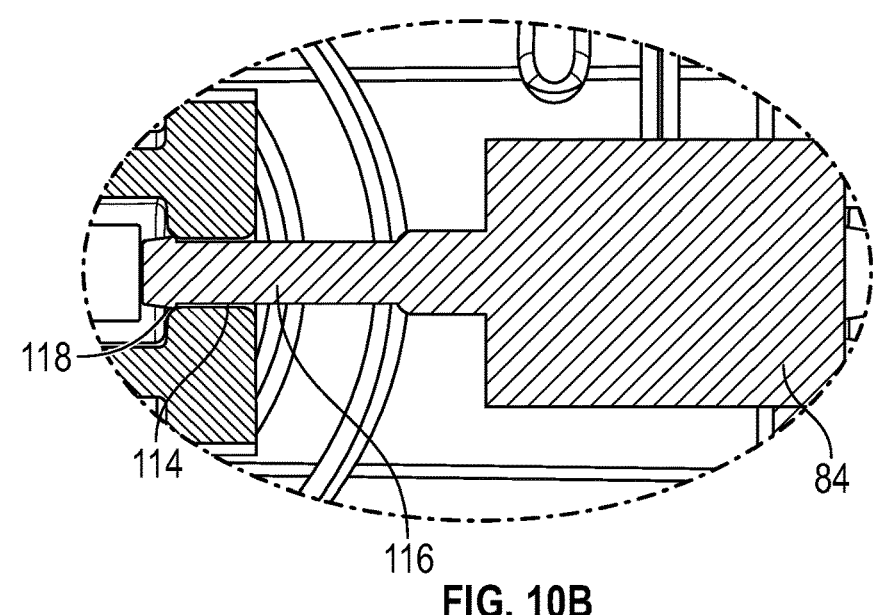
FIG. 10B is an enlarged top cross-sectional view illustrating the other guidewire slider coupled to the needle carrier via the aperture, according to some embodiments.
Figure 10C:
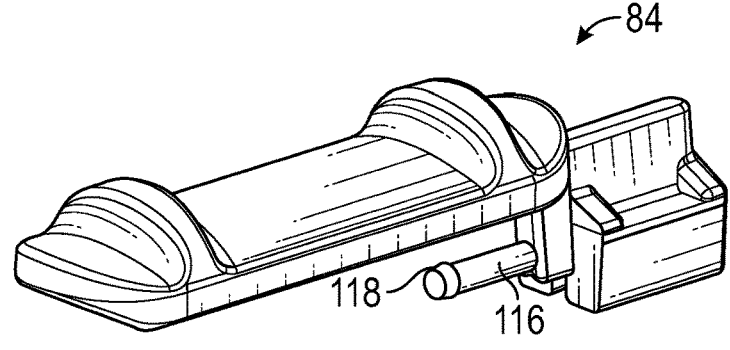
FIG. 10C is an upper perspective view of the other guidewire slider configured to couple to the needle carrier via the aperture, according to some embodiments.

Referring now to FIGS. 10A-10C, in some embodiments, the proximal end of the needle carrier 40 may include an aperture 114. In some embodiments, the guidewire slider 84 may include a distally-extending arm 116 having a protrusion 118, which may be annular. In some embodiments, the protrusion 118 may be configured to snap past the aperture 114 having a smaller diameter than an outer diameter of the protrusion 118 to couple the guidewire slider 84 to the needle carrier 40 in response to distal sliding of the guidewire slider 84. In some embodiments, even if the clinician tries to slide the guidewire slider 84 proximally, the contact between the protrusion 118 and the aperture 114 will resist movement of the guidewire slider 84 until the push-button is pressed releasing the needle 42, decreasing a risk of shearing of the guidewire 46 on the needle 42.

Figures 14A, 14B, 14C:
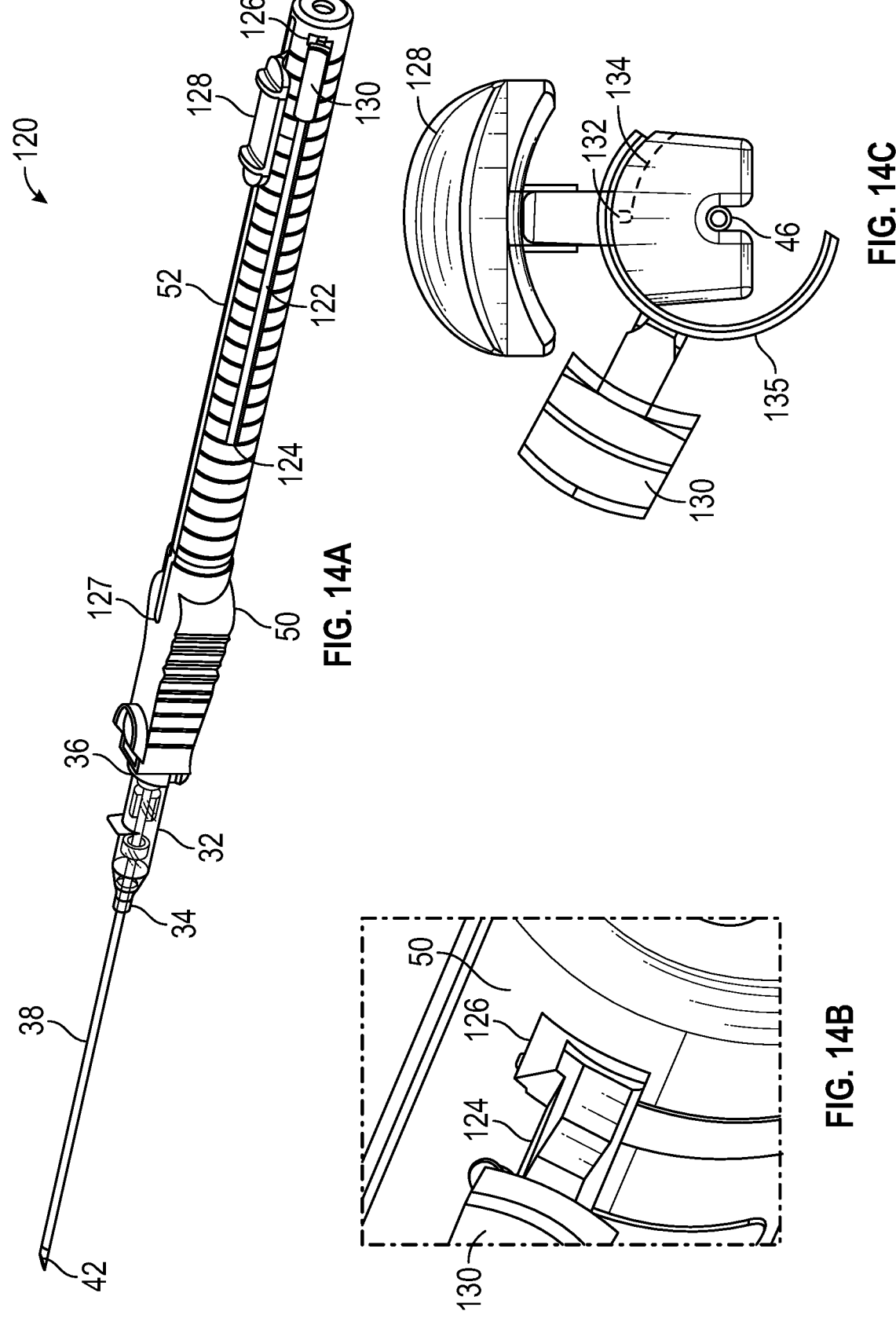
FIG. 14A is an upper perspective view of another example catheter system, according to some embodiments.
FIG. 14B is an enlarged upper perspective view of a portion of the other catheter system, according to some embodiments.
FIG. 14C is a proximal end view of an example additional slider coupled to another example guidewire slider, according to some embodiments.

Referring now to FIGS. 14A-14C, a catheter system 120 may include the catheter hub 32, which may include the distal end 34 and the proximal end 36. In some embodiments, the catheter system 120 may be similar or identical to the catheter system 30 of FIGS. 2-4 and 11-13 in terms of one or more features and/or operation. In some embodiments, the catheter system 120 may include the catheter tube 38 extending distally from the distal end 34 of the catheter hub 32. In some embodiments, the catheter system 120 may include the housing 50 coupled to the catheter hub 32. In some embodiments, the housing 50 may include the slot 52 and another slot 122, or a first slot and a second slot. In some embodiments, a distal end 124 of the other slot 122 may be proximal to a distal end 127 of the slot 52. In some embodiments, a proximal end of the other slot 122 may include a cutout tab 126.

In some embodiments, the catheter system 120 may include the needle carrier 40 disposed within the lumen of the housing 50. In some embodiments, the catheter system 120 may include the needle 42 extending distally from the needle carrier 40 and through the catheter tube 38. In some embodiments, the catheter system 120 may include a guidewire slider 128 configured to slide along the slot 52. In some embodiments, the guidewire slider 128 may be similar or identical to the guidewire slider 44 of FIGS. 2-4 and 11-13 and/or the guidewire slider 84 of FIGS. 5-10 in terms of one or more features and/or operation. In some embodiments, the catheter system 120 may include the guidewire 46 extending distally from the guidewire slider 128.

In some embodiments, the catheter system 120 may include an additional slider 130 configured to slide along the other slot 122. In some embodiments, the guidewire slider 128 and the additional slider 130 may be coupled together such that the guidewire slider 128 and the additional slider 130 are configured to slide distally together along the slot 52 and the other slot 122, respectively. In some embodiments, in response to rotation of the additional slider 130 into the cutout tab 126, the guidewire slider 128 may be configured to uncouple from the additional slider 130.

In some embodiments, in response to uncoupling the guidewire slider 128 from the additional slider 130, the guidewire slider 128 may be configured to slide distally independently of the additional slider 130 and couple to the needle carrier 40. In some embodiments, in response to the guidewire slider 128 being coupled to the needle carrier 40, the guidewire slider 128 and the needle carrier 40 may be configured to slide together proximally. In some embodiments, the push-button or other active safety mechanism may be activated or pushed, which may result in sliding the guidewire slider 44 and the safety slider 48 together proximally towards or into the proximal position, due to pushing by the needle carrier 40.

In some embodiments, the additional slider 130 may include a protrusion 132, and the guidewire slider 128 may include a groove 134. In some embodiments, in response to rotation of the additional slider 130 into the cutout tab 126, the protrusion 132 may be configured to remove from the groove 134 to uncouple the guidewire slider 128 from the additional slider 130. In some embodiments, the protrusion 132 may extend downwardly from an arc-shaped body 135 configured to facilitate smooth rotation with respect to the guidewire slider 128 into the cutout tab 126. In some embodiments, because the distal end of the other slot 122 is proximal to the distal end of the slot 52, this will allow the clinician to test the guidewire 46 by advancing the guidewire slider 128 coupled to the additional slider 130, preventing the guidewire slider 128 from sliding far enough distally to couple to the needle carrier 40.

All examples and conditional language recited herein are intended for pedagogical objects to aid the reader in understanding the invention and the concepts contributed by the inventor to furthering the art and are to be construed as being without limitation to such specifically recited examples and conditions. Although embodiments of the present inventions have been described in detail, it should be understood that the various changes, substitutions, and alterations could be made hereto without departing from the spirit and scope of the invention.

What is claimed:

1. A catheter system, comprising:
    a catheter hub, comprising a distal end and a proximal end;
    a catheter tube extending distally from the distal end of the catheter hub;
    a needle carrier;
    a needle extending distally from the needle carrier and through the catheter tube;
    a guidewire slider;
    a guidewire extending distally from the guidewire slider;
    a safety slider disposed proximal to the guidewire slider and configured to couple to the guidewire slider in response to proximal sliding of the guidewire slider, wherein in response to the guidewire slider being coupled to the safety slider, the guidewire slider and the safety slider are configured to slide together from a proximal position to a distal position, wherein in response to the guidewire slider and the safety slider sliding together from the proximal position to the distal position, the safety slider is configured to couple to a proximal end of the needle carrier, wherein the guidewire slider and the safety slider are configured to return to the proximal position with the needle carrier.

2. The catheter system of claim 1, further comprising a housing, wherein the housing comprises a slot, wherein the guidewire slider and the safety slider extend through the slot and are configured to slide along the slot.

3. The catheter system of claim 2, wherein the slot comprises a bump, wherein the safety slider comprises another bump, wherein when the guidewire slider and the safety slider are in the proximal position, the bump of the slot is distal to and contacting the other bump of the safety slider to provide resistance to distal sliding of the safety slider.

4. The catheter system of claim 1, wherein the safety slider comprises a first arm and a second arm opposite the first arm, wherein a distal end of the first arm comprises a first hook feature, wherein a distal end of the second arm comprises a second hook feature, wherein the proximal end of the needle carrier comprises a first flange and a second flange, wherein in response to the guidewire slider and the safety slider sliding together from the proximal position to the distal position, the first hook feature and the second hook feature are configured to couple to the first flange and the second flange, respectively, to couple the safety slider to the proximal end of the needle carrier.

5. The catheter system of claim 1, wherein the safety slider comprises a first arm, a second arm opposite the first arm, and a boss in between the first arm and the second arm, wherein an upper surface of the guidewire slider comprises a groove, wherein when the safety slider is coupled to the guidewire slider, the boss sits within the groove.

6. The catheter system of claim 1, wherein the safety slider comprises a first arm and a second arm opposite the firm arm, wherein the first arm comprises a first snap feature and the second arm comprises a second snap feature, wherein the guidewire slider comprises a first corresponding snap feature and a second corresponding snap feature, wherein the first snap feature and the second snap feature are configured to snap past the first corresponding snap feature and the second corresponding snap feature, respectively, to couple the safety slider with the guidewire slider in response to the proximal sliding of the guidewire slider.

7. The catheter system of claim 6, wherein an internal surface of the first arm comprises the first snap feature and an internal surface of the second arm comprises the second snap feature, wherein a first side of the guidewire slider comprises the first corresponding snap feature and a second side of the guidewire slider comprises the second corresponding snap feature.

8. The catheter system of claim 6, wherein the safety slider further comprises a boss, wherein a first side of the boss comprises the first snap feature and a second side of the boss comprises the second snap feature, wherein a first internal surface of the guidewire slider comprises the first corresponding snap feature and a second internal surface of the guidewire slider comprises the second corresponding snap feature.

9. The catheter system of claim 8, wherein a distal end of the boss comprises a shape corresponding to a shape of the guidewire slider between the first corresponding snap feature and the second corresponding snap feature.

* * * * *